US012655375B2

(12) United States Patent
Jing et al.

(10) Patent No.: US 12,655,375 B2
(45) Date of Patent: Jun. 16, 2026

(54) AUTOMATED CELL CULTURING

(71) Applicant: Huacells Corporation, Natick, MA (US)

(72) Inventors: Jie Jing, Milton, MA (US); Kenneth A. Collins, Nashua, NH (US); Fang Yuan, Framingham, MA (US); Zhonghua Zhang, Winchester, MA (US); Lawrence St. George, Sudbury, MA (US); Jeffery J. Driscoll, Framingham, MA (US); Weijia Tan, Malden, MA (US); Hao Cai, Brookline, MA (US); Dongping Lin, Las Vegas, NV (US); Jian Cheng, Beijing (CN)

(73) Assignee: Huacells Corporation, Natick, MA (US)

(*) Notice: Subject to any disclaimer, the term of this patent is extended or adjusted under 35 U.S.C. 154(b) by 263 days.

(21) Appl. No.: 16/229,303

(22) Filed: Dec. 21, 2018

(65) Prior Publication Data

US 2019/0352589 A1 Nov. 21, 2019

Related U.S. Application Data

(60) Provisional application No. 62/673,484, filed on May 18, 2018.

(51) Int. Cl.
*C12M 1/00* (2006.01)
*C12M 1/02* (2006.01)
(Continued)

(52) U.S. Cl.
CPC ............ *C12M 21/00* (2013.01); *C12M 27/00* (2013.01); *C12M 41/14* (2013.01); *C12M 41/26* (2013.01); *C12M 41/36* (2013.01); *C12M 41/48* (2013.01)

(58) Field of Classification Search
CPC ...... C12M 21/00; C12M 41/36; C12M 41/48; C12M 27/00; C12M 41/26; C12M 41/14; C12M 41/12; C12M 29/00
See application file for complete search history.

(56) References Cited

U.S. PATENT DOCUMENTS 4,918,019 A     4/1990   Guinn
5,424,209 A  *  6/1995   Kearney ................ C12M 41/48
                                             435/286.5

(Continued)

FOREIGN PATENT DOCUMENTS

CN      104789472 A  *  7/2015  ............... C12N 1/12
CN      105925481      9/2016

(Continued)

OTHER PUBLICATIONS

Yu et al, "English machine translation of CN 107043701 A". Translated on Mar. 27, 2021.*

(Continued)

*Primary Examiner* — Liban M Hassan
(74) *Attorney, Agent, or Firm* — Fish & Richardson P.C.

(57) ABSTRACT

An automated cell culture system includes a cell culture reactor including a housing; a fluidic circuit for cell culture media, the fluidic circuit disposed in an interior of the housing. The fluidic circuit includes a culture vessel for culturing cells in the cell culture media, a reservoir for the cell culture media, the reservoir fluidically connected to the culture vessel, and a pump configured to pump the cell culture media in the fluidic circuit. The automated cell culture system includes one or more sensors disposed in the interior of the housing, each sensor configured to detect a parameter of one or more of (1) the cell culture media in the fluidic circuit and (2) an environment in the interior of the housing; and a computing device configured to automati- (Continued)

cally control operation of the cell culture reactor based on one or more of the detected parameters.

12 Claims, 27 Drawing Sheets

(51) Int. Cl.
  *C12M 1/34* (2006.01)
  *C12M 1/36* (2006.01)

(56) References Cited

U.S. PATENT DOCUMENTS

| | | | | |
|---|---|---|---|---|
| 6,673,008 | B1 * | 1/2004 | Thompson | C12M 21/06 |
| | | | | 600/35 |
| 7,410,792 | B2 * | 8/2008 | Vilendrer | C12M 35/04 |
| | | | | 435/284.1 |
| 2002/0146817 | A1 | 10/2002 | Cannon et al. | |
| 2003/0175164 | A1 * | 9/2003 | Micklash, II | B01L 3/50255 |
| | | | | 422/131 |
| 2005/0002910 | A1 * | 1/2005 | Wolfinbarger | C12M 35/02 |
| | | | | 435/366 |
| 2006/0194193 | A1 * | 8/2006 | Tsuruta | C12M 29/10 |
| | | | | 435/4 |
| 2009/0215022 | A1 | 8/2009 | Page et al. | |
| 2010/0075406 | A1 * | 3/2010 | Tanaka | C12M 27/02 |
| | | | | 435/287.1 |
| 2011/0300622 | A1 * | 12/2011 | Barzilai | B01L 9/523 |
| | | | | 901/14 |
| 2013/0058907 | A1 | 3/2013 | Wojciechowski et al. | |
| 2015/0017711 | A1 * | 1/2015 | Bennett | C12M 41/44 |
| | | | | 435/286.2 |
| 2015/0111252 | A1 | 4/2015 | Hirschel et al. | |
| 2015/0175950 | A1 | 6/2015 | Hirschel et al. | |
| 2016/0032358 | A1 * | 2/2016 | Buse | B01L 7/5255 |
| | | | | 435/6.12 |
| 2016/0145563 | A1 * | 5/2016 | Berteau | C12M 41/48 |
| | | | | 137/15.01 |

FOREIGN PATENT DOCUMENTS

| | | | | |
|---|---|---|---|---|
| CN | 106467892 A | 3/2017 | | |
| CN | 106566772 | 4/2017 | | |
| CN | 107012094 | 8/2017 | | |
| CN | 107012094 A | 8/2017 | | |
| CN | 107043701 | 8/2017 | | |
| JP | 05123156 A * | 5/1993 | | C12M 29/26 |
| WO | WO-2004058046 A2 * | 7/2004 | | A61M 1/02 |
| WO | WO 2017004592 | 1/2017 | | |
| WO | WO-2017187680 A1 * | 11/2017 | | C12M 1/00 |
| WO | WO 2018038214 | 6/2019 | | |

OTHER PUBLICATIONS

PCT International Search Report and Written Opinion in International Application No. PCT/CN2019/0867169, dated Aug. 19, 2019, 10 pages.

EP European Search Report in European Appln. No. 19803661 .8, dated Apr. 21, 2021, 7 pages.

PCT International Preliminary Report on Patentability in International Appln. No. PCT/CN2019/087169, dated Nov. 24, 2020, 5 pages.

CN Office Action in Chinese Appln. No. 201910410428.6, dated Jun. 6, 2022, 22 pages (with English translation).

JP Japanese Office Action in Japanese Appln. No. 2020-563557, dated Oct. 19, 2022, 6 pages (with English translation).

JP Japanese Office Action in Japanese Appln. No. 2020-563557, dated Jun. 28, 2023, 6 pages (with English translation).

thermofisher.com, "All you need to know about passaging cultured cells," Aug. 11, 2016, retrieved Jul. 28, 2023 from URL <https://www.thermofisher.com/blog/learning-at-the-bench/guidelines-for-maintaining-cultured-cells/>, 9 pages.

* cited by examiner

Fig. 26A
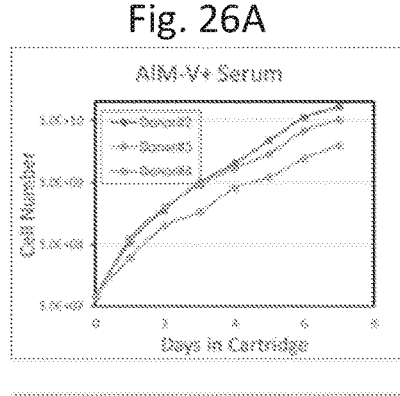
Fig. 26B
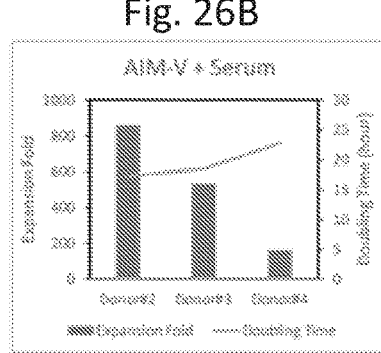
Fig. 26C
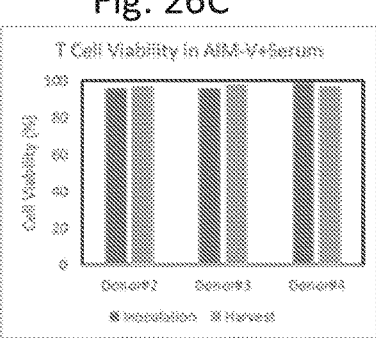
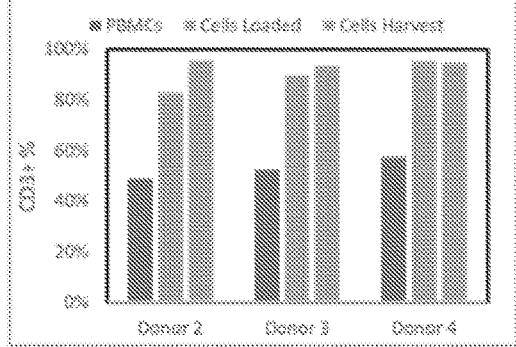
Fig. 26D
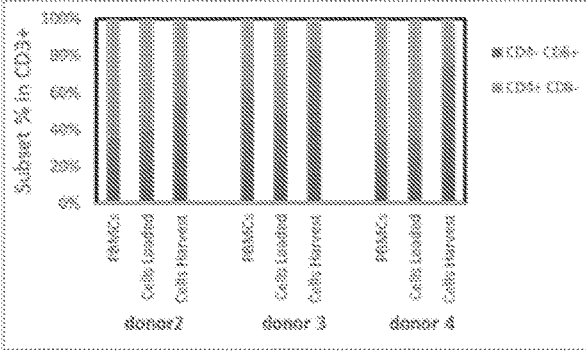
Fig. 26E

AUTOMATED CELL CULTURING

CLAIM OF PRIORITY

This application claims priority to U.S. Patent Application Ser. No. 62/673,484, filed on May 18, 2018, the contents of which are incorporated here by reference in their entirety.

BACKGROUND

Cell culture can be used to increase cell populations. For instance, T-cells can be harvested from a person's blood and cultured externally from the person's body to rapidly increase the number of T-cells. The cultured T-cells can be activated to become more effective in their disease fighting role through exposure to materials such as antigens or immunological stimulants such as cytokines. Expanded and activated T-cells can be transfused back into the person to improve the person's immune response. Cell culture can also be used for other types of cells, such as stem cells or other types of cells; or for production of cell derived products, e.g., for production of proteins, eukaryotic cell derived products, or other products.

SUMMARY

In an aspect, an automated cell culture system includes a cell culture reactor including a housing; a fluidic circuit for cell culture media, the fluidic circuit disposed in an interior of the housing. The fluidic circuit includes a culture vessel for culturing cells in the cell culture media, a reservoir for the cell culture media, the reservoir fluidically connected to the culture vessel, and a pump configured to pump the cell culture media in the fluidic circuit. The automated cell culture system includes one or more sensors disposed in the interior of the housing, each sensor configured to detect a parameter of one or more of (1) the cell culture media in the fluidic circuit and (2) an environment in the interior of the housing; and a computing device configured to automatically control operation of the cell culture reactor based on one or more of the detected parameters.

Embodiments can include one or more of the following features.

The computing device is configured to control operation of the cell culture reactor based on a comparison between each of one or more of the detected parameters and respective thresholds. The threshold for at least one of the detected parameters is based on a phase of the cell culturing. The computing device is configured to determine the phase of the cell culturing based on one or more of the detected parameters.

The sensor includes a reservoir sensor configured to detect an amount of the cell culture media in the reservoir. The reservoir sensor includes a mass sensor. The reservoir sensor includes a strain gauge.

The automated cell culture system includes a rotational mount for the cell culture vessel.

The automated cell culture system includes a supply system including a supply line, a first end of the supply line being connected to the fluidic circuit, and a second end of the supply line connectable to a source of cell culture media; and a supply pump coupled to the supply line. The supply system includes a temperature control system including a housing, an interior space of the housing configured to hold the source of cell culture media; and a temperature control module configured to cool or warm the interior space of the housing. The computing device is configured to control operation of the supply pump based on an amount of cell culture media in the reservoir. The computing device is configured to control operation of the supply pump based on the amount of cell culture media in the reservoir being less than a threshold amount. The computing device is configured to control operation of the supply pump based on a target amount of cell culture media in the reservoir, the target amount being based on a phase of the cell culturing. The computing device is configured to control operation of the supply pump based on a pH of the cell culture media in the fluidic circuit.

The one or more sensors include a pH sensor configured to detect a pH of the cell culture media in the fluidic circuit. The pH sensor includes a colorimetric pH sensor. The pH sensor includes an ionic pH sensor.

The automated cell culture system includes a heater disposed in an interior of the housing. The computing device is configured to control operation of the heater based on a temperature at an exterior of the culture vessel.

The automated cell culture device includes a valve in the housing, in which the computing device is configured to control operation of the valve based on a concentration of gas in the interior of the housing.

The automated cell culture system includes a gas source fluidically coupled to the interior of the housing; and a gas flow control device coupled to the gas source. The computing device is configured to control operation of the gas flow control device based on one or more of the detected parameters. The gas flow control device includes a mass flow controller. The gas flow control device includes a metered valve. The computing device is configured to control operation of the gas flow control device based on a comparison between (i) a deviation between a concentration of a gas in the interior of the housing and a threshold concentration and (ii) a target deviation. The one or more sensors a gas sensor configured to detect a concentration of a gas in the interior of the housing. The computing device is configured to control operation of the gas flow control device based on the detected concentration of gas. The computing device is configured to control operation of the gas flow control device based on a pH of the cell culture media in the fluidic circuit. The computing device is configured to control operation of the gas flow control device based on an amount of dissolved oxygen in the cell culture media in the fluidic circuit.

The one or more sensors include a dissolved oxygen sensor configured to detect an amount of oxygen dissolved in the cell culture media in the fluidic circuit.

The one or more sensors include a glucose sensor configured to detect an amount of glucose in the cell culture media in the fluidic circuit.

The one or more sensors include a lactic acid sensor configured to detect an amount of lactic acid in the cell culture media in the fluidic circuit.

The computing device is configured to control operation of the cell culture reactor based on a phase of the cell culture in the culture vessel. The computing device is configured to determine the phase of the cell culture based on one or more of (i) one or more of the detected parameters and (ii) a history of one or more of the detected parameters. The computing device is configured to control operation of the pump based on the phase of the cell culture. The automated cell culture system includes a supply system including a supply line, a first end of the supply line being connected to the fluidic circuit, and a second end of the supply line connectable to a source of cell culture media; and a supply pump coupled to the supply line; and in which the computing device is configured to control operation of the supply pump based on the phase of the cell culture.

The culture vessel includes a hollow fiber cartridge.

The automated cell culture system includes a waste line, a first end of the waste line being connected to the fluidic circuit, and a second end of the waste line connectable to a waste media reservoir; and a waste pump coupled to the waste line.

The automated cell culture system includes a user interface, wherein the computing device is configured to cause an output on the user interface indicative of one or more of the detected parameters. The user interface includes a graphical user interface. The user interface includes a touch sensitive user interface.

The computing system is configured to provide information indicative of one or more of the detected parameters to a remote computing device.

The computing device is configured to cause output of an alert based on one or more of the detected parameters.

The automated cell culture system includes a data storage configured to store information indicative of one or more of the detected parameters.

The computing device is configured to provide to a data storage through a network connection, information indicative of one or more of the detected parameters.

In an aspect, a method for culturing cells includes incubating cells in a cell culture reactor, including flowing cell culture media in a fluidic circuit disposed in an interior of the cell culture reactor, including pumping cell culture media from a reservoir for the cell culture media to a culture vessel for culturing the cells in the cell culture media. The method includes detecting, by each of one or more sensors disposed in the interior of the cell culture reactor, a parameter of one or more of (1) the cell culture media in the fluidic circuit and (2) an environment in the interior of the cell culture reactor; and based on one or more of the detected parameters, automatically, by a computing device, controlling operation of the cell culture reactor.

Embodiments can include one or more of the following features.

Controlling operation of the cell culture reactor includes comparing each of the detected parameters to a respective threshold; and controlling operation of the cell culture reactor based on the comparison. The threshold for at least one of the detected parameters is based on a phase of the cell culturing. The method includes determining the phase of the cell culturing based on one or more of (i) one or more of the detected parameters and (ii) a history of one or more of the detected parameters.

Detecting a parameter includes detecting an amount of cell culture media in the reservoir.

The method includes rotating the cell culture vessel.

Controlling operation of the cell culture reactor includes controlling operation of a supply pump to pump cell culture media from a source of cell culture media into the fluidic circuit. The method includes controlling a temperature of the source of cell culture media. The method includes warming the cell culture media pumped from the source of cell culture media into the fluidic circuit. The method includes controlling operation of the supply pump based on an amount of cell culture media in the reservoir. The method includes controlling operation of the supply pump based on the amount of cell culture media in the reservoir being less than a threshold amount. The method includes controlling operation of the supply pump based on a target amount of cell culture media in the reservoir, the target amount being based on a phase of the cell culturing. The method includes controlling operation of the supply pump based on a pH of the cell culture media in the fluidic circuit.

The method includes including detecting a pH of the cell culture media in the fluidic circuit.

Controlling operation of the cell culture reactor includes controlling a heater based on a temperature in the cell culture reactor.

Controlling operation of the cell culture reactor includes controlling operation of a gas flow control device coupled to a gas source. The method includes detecting a concentration of gas in the interior of the cell culture reactor; and controlling operation of the gas flow control device based on the detected concentration of gas. The method includes controlling operation of the gas flow control device based on a comparison between (i) a deviation between the concentration of a gas in the interior of the cell culture reactor and a threshold concentration and (ii) a target deviation. The method includes controlling operation of the gas flow control device based on a pH of the cell culture media in the fluidic circuit.

The method includes controlling operation of a valve in a housing of the cell culture reactor based on a detected concentration of gas in the interior of the cell culture reactor.

The method includes controlling operation of the cell culture reactor based on a phase of the cell culture in the culture vessel. The method includes determining the phase of the cell culture based on one or more of the detected parameters. The method includes controlling the pumping of cell culture media in the fluidic circuit based on the phase of the cell culture. The method includes controlling operation of a supply pump to pump cell culture media from a source of cell culture media into the fluidic circuit based on the phase of the cell culture.

The method includes causing output of an alert based on one or more of the detected parameters.

The method includes causing output of information indicative of one or more of the detected parameters on a user interface. Causing output of the information on the user interface includes causing output of the information on a graphical user interface. The method includes receiving an input through the user interface; and controlling operation of the cell culture reactor based further on the received input.

The method includes storing information indicative of one or more of the detected parameters in a data storage.

The method includes providing to a data storage through a network connection, information indicative of one or more of the detected parameters.

The method includes controlling operation of the computing device by a remote computing device connected to the computing device by a network connection.

Automated cell culture systems can have one or more of the following advantages. Cells can be cultured under automated, computer control in a process that does not involve labor-intensive human interaction and that has a low risk of human error and contamination. In the automated cell culture system, a closed cell culture process can be facilitated while reducing or minimizing human interference, thereby facilitating scalable, cost-effective, clinical-grade cell manufacturing. The automated cell culture system can be implemented as a hermetically sealed cell culture fluidic circuit a compact benchtop environment, which takes up little space and is cost effective to purchase and operate.

BRIEF DESCRIPTION OF DRAWINGS

FIGS. 26A-26E are plots of cell expansion.

DETAILED DESCRIPTION

We describe here an automated cell culture system for automated, computer-controlled culture, transfection, and expansion of cells, such as suspension or adherent cells, e.g., T cells, stem cells, or other types of cells. The conditions of the cell culture environment in the automated cell culture system can be dynamically and automatically adjusted responsive to real time sensor monitoring to maintain steady state conditions in the cell culture media, e.g., to maintain parameters such as media volume, flow pressure, flow speed, pH, dissolved oxygen, glucose concentration, lactate concentration, or other parameters within preset bounds. The ability to maintain steady state conditions in the cell culture media helps to reduce physiochemical stress on the cultured cells, thereby improving cell culture efficiency and the viability of the cultured cells. Product harvested from the automated cell culture system can include the cells themselves or byproducts of the cultured cells, such as proteins, viruses, antibody, or other cell byproducts.

A variety of cell culture processes can be carried out using the automated cell culture system described here, including ambient cell culture; hypoxic cell culture; culture in human or animal-sourced serum; culture in serum-free media; culturing of T lymphocytes, red blood cells, induced pluripotent stem cells, natural killer cells and cell lines, or other types of cells; or other processes. The automated cell culture system described here enables the activation and/or expansion of viable cells with tunable growth rate and high harvest rate.

Figure 1:
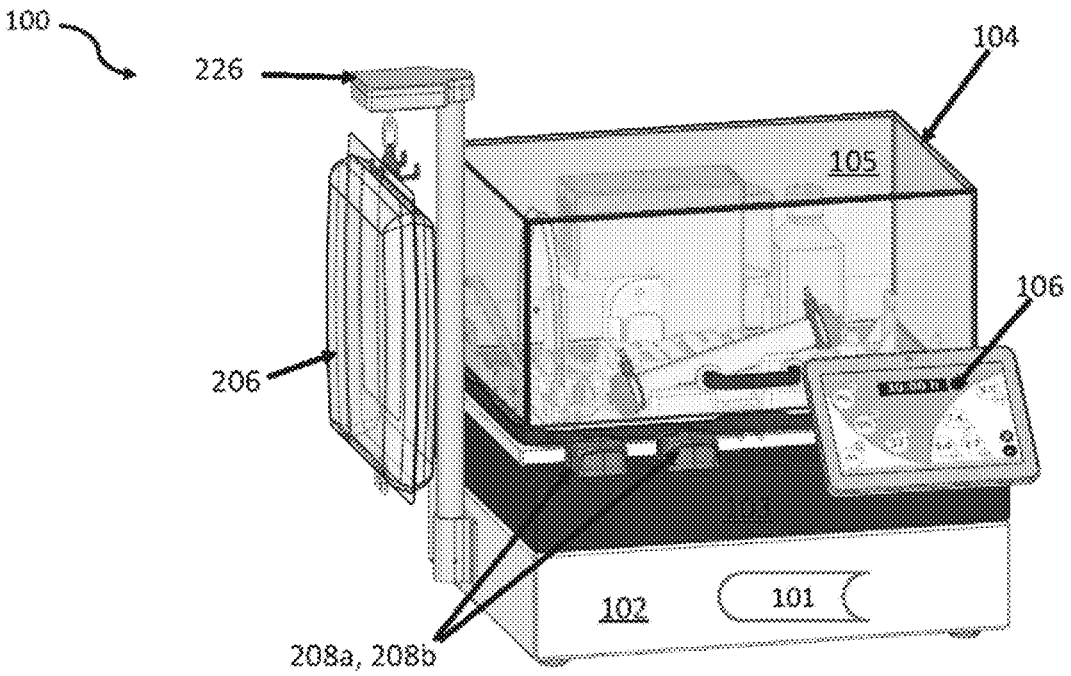
FIGS. 1 and 2 are diagrams of a cell culture system.

Referring to FIG. 1, an automated cell culture system 100 is an integrated device for culturing cells under automated, computer control. A base portion 102 of the automated cell culture system 100 houses a computing device 101, such as one or more microprocessors coupled to a memory, that controls the operation of the automated cell culture system 100. A clamp cover 103 can clamp the base portion 102 closed and mechanically locked, e.g., to help prevent accidental or unauthorized access to the computing device 101.

A reactor portion 104 of the automated cell culture system 100 includes a housing 105 defining an interior, incubation space in which the cell culturing takes place. The housing can be hermetically sealed. For instance, the housing can be fitted to the clamp cover 103 by a silicone gasket. The sealed housing can help prevent gas leakage, e.g., to enable efficient control of gas concentration in the interior of the housing 105 and efficient gas usage, and to enable efficient temperature control. The reactor portion 104 houses a cell culture vessel in which cells, such as T cells, can be efficiently cultured in cell culture media in an environment monitored and controlled by the computing device. The reactor portion 104 can house one or more sensors, coupled to the computing device of the automated cell culture system 100. The sensors can detect parameters of the culture environment, such as temperature, pH of the cell culture media, concentration of gases such as oxygen or carbon dioxide in the atmosphere in the reactor portion 104, concentration or partial pressure of gases such as oxygen dissolved in the cell culture media, concentration of sugars such as glucose, concentration of cell culture byproducts such as lactate, or other parameters of the cell culture environment. The reactor portion 104 can house one or more components operable under automatic control by the computing device of the automated cell culture system 100, such as heating components, gas flow controllers, pumps, or other components of the automated cell culture system 100. For instance, the computing device of the automated cell culture system 100 can automatically control operation of one or more components in the reactor portion 104 in a closed loop feedback system based on parameters of the culture environment detected by one or more sensors in the reactor portion.

The automatic monitoring and control of parameters of the culture environment can help achieve efficient cell culturing. For instance, components of the automated cell culture system can be controlled in real time responsive to changes in parameters of the cell culturing environment, e.g., without waiting for a user to manually operate the system or manually input control instructions. The real time control of the system responsive to real time monitoring enables target parameters to be consistently maintained, such as a target amount of cell culture media in the system, a target concentration of gases, a target concentration of culturing reagents such as growth factor, a target temperature, a target pH, or other parameters. The ability to maintain parameters consistently at target values throughout the cell culturing process can help improve efficiency of the culturing.

The automatic monitoring and control of parameters of the culture environment can also help achieve efficient use of resources, such as growth factor, thus reducing material costs associated with cell culturing. For instance, based on real time monitoring of parameters of the culturing environment, the phase of the cell culturing process can be determined. Target values for certain parameters may vary depending on the phase of the cell culturing process. These parameters can be monitored and adjusted in real time responsive to a dynamic determination of the phase of the cell culturing process.

In the example of FIG. 1, the computing device 101 housed in the base portion 102 of the automated cell culture system 100 controls the operation of the automated cell culture device 100, e.g., receiving signals from the one or more sensors housed in the reactor portion 104 and controlling operation of the one or more components housed in the reactor portion 104. In some examples, the automated cell culture device 100 can be connected through a wired or wireless connection to a remote computing device, such as a laptop or desktop computer, a server, or a mobile computing device, and the remote computing device can monitor and/or control the operation of the automated cell culture device 100. In some examples, a microprocessor-based controller housed in the base portion 102 of the automated cell culture system 100, or connected to the automated cell culture system, can monitor and/or control the operation of the automated cell culture system. As used herein, terms such as "computer controlled" and "controlled by the computing device of the automated cell culture system" refer to control of the automated cell culture system 100 by a computing device or microprocessor-based controller housed in the automated cell culture system 100 or by a remote computing device or microprocessor-based controller.

A display 106, such as a liquid crystal display (LCD), can be mounted or integrated on the automated cell culture system 100, such as on a housing of the clamp cover 103 or on a housing of the reactor portion 104. The display 106 can be controlled by the computing system to display information indicative of parameters of the cell culture environment, such as real time readings from one or more of the sensors. The display 106 can be controlled by the computing system to display status alerts, e.g., to indicate that a parameter has exceeded or fallen below a threshold. In some examples, information can be displayed on a remote display, such as a display on a remote computing device, e.g., a laptop or desktop computer or a mobile computing device, coupled to the computing device of the automated cell culture system 100 by a wired or wireless connection. In some examples, status information can be provided in other ways, such as by visual indicators (e.g., one or more lights that blink or light up in a given pattern to communicate status information) or audible indicators (e.g., alarms or spoken words to communicate status information).

In some examples, the display 106 can be an interactive display, such as a touch sensitive display, capable of receiving input from a user and providing a signal indicative of the received input to the computing system. For instance, the display 106 can be configured to receive information or instructions from a user, e.g., instructions to set threshold levels for parameters of the cell culture environment, instructions for operation of one or more components in the reactor portion 104, information identifying or characterizing the cells to be cultured in the automated cell culture system 100, or other types of information or instructions. In some examples, information or instructions can be received from a remote computing device, e.g., a laptop or desktop computer or a mobile computing device coupled to the computing device of the automated cell culture system 100 by a wired or wireless connection. The information can be stored in a centralized data storage, such as cloud-based data storage, or in a distributed data storage system. The information can be analyzed, e.g., to the improve system performance, to tailor parameter threshold settings, or for other objectives. For instance, using the collected information, an artificial intelligence based cell culture algorithm can be developed or updated and applied to the automated cell culture system.

Figure 2:
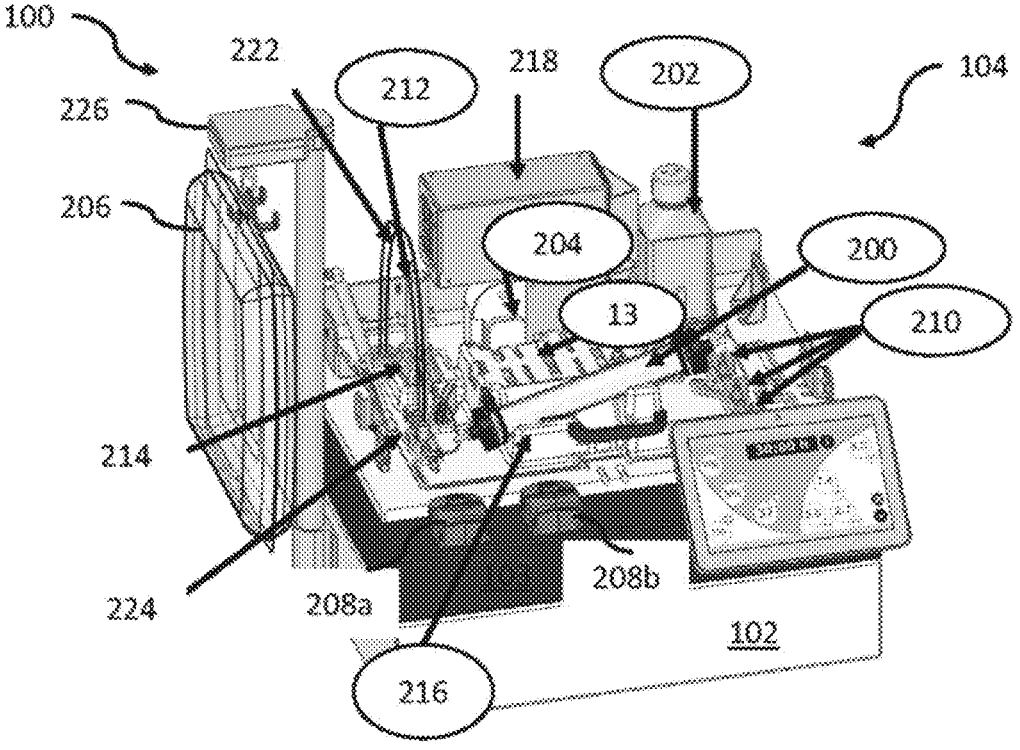
Figure 4:
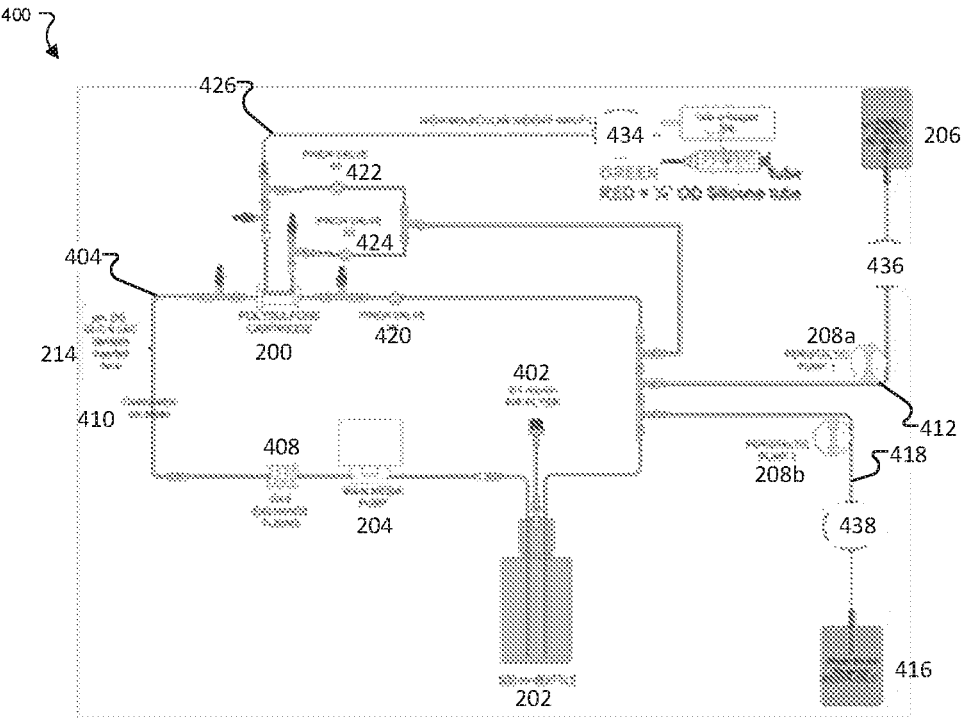
FIG. 4 is a diagram of a fluidic circuit.

Referring to FIG. 2, in the interior of the reactor portion 104 of the automated cell culture system 100, cells are cultured in a culture vessel 200, such as a cartridge, e.g., a hollow fiber cartridge. The culture vessel 200 is fluidically connected to a reservoir 202, such as a bottle, by tubing (not shown), e.g., silicone tubing. A pump 204, such as a peristaltic or pulsatile pump, pumps cell culture media from the reservoir 202 through a first portion of the tubing to an input end of the culture vessel 200 and from an output end of the culture vessel 200 through a second portion of the tubing and back to the reservoir in a fluidic circuit (e.g., a fluidic circuit 400 as shown in FIG. 4, discussed below).

Fresh cell culture media can be introduced into the fluidic circuit from a fresh media source 206 through a supply line. For instance, a pump 208*a*, such as a peristaltic pump, and one or more valves 210, such as pinch valves, can be operable under computer control to pump fresh cell culture from the fresh media source 206 through the supply line and into the fluidic circuit. Cell culture media can be pumped out of the fluidic circuit along a waste line to a waste destination (not shown) by a pump 208*b*, such as a peristaltic pump. The pumps 208*a*, 208*b* can be automatically operable under control of the computing system of the automated cell culture system. In some examples, pumping fresh cell culture media into the fluidic circuit from the fresh media source 206 can occur substantially concurrently with pumping cell culture media out of the fluidic circuit to the waste destination to avoid providing more cell culture media than the capacity of the fluidic circuit. In some examples, cell culture media is pumped into the fluidic circuit from the fresh media source 206 at a higher flow rate than cell culture media is pumped out of the fluidic circuit to the waste destination, e.g., to increase the volume of cell culture media in the fluidic circuit. In some examples, cell culture media is pumped into the fluidic circuit from the fresh media source 206 at a lower flow rate than cell culture media is pumped out of the fluidic circuit to the waste destination, e.g., to decrease the volume of cell culture media in the fluidic circuit.

One or more sensors housed in the reactor portion 104 of the automated cell culture system 100 are configured to sense parameters of the culture environment in real time and provide signals indicative of the sensed parameters to a local controller, to the computing device of the automated cell culture system 100, or both. The sensors can be in wired or wireless communication with the computing device of the automated cell culture system. By the culture environment, we mean the cell culture media and the atmosphere in the interior of the housing of the reactor portion 104 of the automated cell culture system 100. The sensors can include temperature sensors, pH sensors, dissolved gas sensors, atmospheric gas sensors, glucose sensors, lactate sensors, fluid mass or volume sensors, or other types of sensors. The controller or computing device 100 can automatically, without real time user input, control operation of one or more components of the automated cell culture system, such as heaters, gas flow controllers, pumps, or other components, responsive to the sensed parameters. The real time adjustment of parameters, e.g., in a closed loop feedback system, can enable time- and resource-efficient cell culture. In some examples, the computing device 100 can determine, based on the sensed parameters or historical records of the sensed parameters or both, the phase of the cell culturing, and thereby can control operation of one or more components of the automated cell culture system 100 based on the phase of the cell culturing. The computing device 100 can cause alerts, such as one or more of visual alerts and audio alerts, to be output on a user interface, such as on the display 106, e.g., when a sensed parameter exceeds or falls below a threshold, when a change in the phase of the cell culturing is identified, or for other reasons.

In some examples, one or more pH sensors 212, 214 can be housed in the reactor portion 104 of the automated cell culture system 100 and positioned to detect the pH of the cell culture media in the fluidic circuit. For instance, the pH sensors 212, 214 can be positioned to detect the pH of cell culture media in the tubing between the reservoir 202 and the input end of the culture vessel 200, in the tubing between the output end of the culture vessel 200 and the reservoir 202, or elsewhere along the fluidic circuit. In the example of FIG. 2, the pH sensor 212 is an ionic pH sensor that detects pH of a fluid based on the photoluminescence quenching of the fluid, and the pH sensor 214 is a colorimetric pH sensor that detects pH of a fluid based on a sensed hue of the fluid. Other types of pH sensors can also be used. In some examples, only a single pH sensor is used.

The pH sensors 212, 214 can be in wired or wireless communication with the computing system of the automated cell culture system 100. For instance, when the pH of the cell culture media falls below a threshold pH (e.g., a threshold value set by a user, such as a pH below which cell culturing is less efficient or a pH below which the cell culture media is harmful to the cultured cells), the computing system of the automated cell culture system 100 can automatically control the pump 208b to pump current cell culture media out of the fluidic circuit to a waste destination, can automatically control the pump 208a to pump fresh cell culture media into the fluidic circuit from the fresh media source 206, can automatically control a carbon dioxide gas mass flow controller to decrease the concentration of carbon dioxide in the atmosphere in the interior of the reactor portion, or can automatically control another component of the automated cell culture system 100. The computing system can cause an alert to be output on a user interface, such as on the display 106, e.g., when the pH falls below the threshold pH.

The automated cell culture system 100 can include a thermal subsystem housed in the reactor portion 104 for monitoring and control of the temperature in the interior of the reactor portion 104 of the automated cell culture system 100. A temperature sensor 216 detects the temperature at the exterior of the culture vessel 200, e.g., as a proxy for the temperature of the cell culture media in the fluidic circuit. One or more heating devices housed in a heating tower 218, such as a heater, a fan, or both, are operable under control by the computing system of the automated cell culture system to control the temperature at the exterior of the culture vessel 200, e.g., in a closed loop feedback system based on the temperature detected by the temperature sensor 216. The computing system can cause an alert to be output on a user interface, such as on the display 106, e.g., when the temperature falls outside of a preset temperature range. The thermal subsystem is discussed in more detail with respect to FIG. 9.

The automated cell culture system 100 can include a gas subsystem housed in the reactor portion 104 for monitoring and control of the concentration of one or more gases, such as one or more of oxygen, carbon dioxide, or another type of gas, in the interior of the reactor portion of the automated cell culture system. One or more gas sensors, such as an oxygen sensor, a carbon dioxide sensor, or a sensor for another type of gas, detect gas concentrations in the atmosphere in the interior of the reactor portion. A dissolved oxygen sensor 222 can detect the concentration of oxygen dissolved in the cell culture media. For instance, the dissolved oxygen sensor can determine the amount of oxygen present in the cell culture media surrounding the sensor based on fluorescent quenching of light.

The gas sensors can be in wired or wireless communication with the computing system of the automated cell culture system 100. The computing system can control one or more mass flow controllers to provide a flow of gas, such as carbon dioxide or nitrogen, from a gas source to the interior of the reactor portion of the automated cell culture system responsive to the concentration of gas, such as carbon dioxide or oxygen, in the reactor portion, e.g., in a closed loop feedback system. In some examples, the computing system can control the mass flow controllers based on the detected concentration of dissolved gas, such as dissolved oxygen, in the cell culture media in the fluidic circuit. The computing system can cause an alert to be output on a user interface, such as on the display 106, e.g., when the concentration of one of the monitored gases falls outside of a preset concentration range. The gas subsystem is discussed in more detail with respect to FIG. 10.

The automated cell culture system 100 can include a glucose sensor 224, such as a microelectromechanical system (MEMS)-circuit mounted, enzyme based sensor, that detects an amount of glucose in the cell culture media. The automated cell culture system 100 can include a lactate sensor that detects an amount of lactate in the cell culture media. In some examples, a single sensor can be configured to detect both glucose and lactate. The glucose sensor 224, lactate sensor, or other sensors are housed in the reactor portion 104 of the automated cell culture system 100 and can be in wired or wireless communication with the computing system of the automated cell culture system for monitoring glucose consumption and lactate production in the cell culture media, e.g., as an indication of cell growth. The computing system can cause an alert to be output on a user interface, such as on the display 106, e.g., when the concentration of glucose or lactate falls outside of a preset concentration range.

The automated cell culture system 100 can include a fluid amount sensor (not shown), housed in the reactor portion 104, to detect an amount, such as a mass or volume, of cell culture media in the reservoir 202. The fluid amount sensor can be a mass sensor, such as a strain gauge, that can detect the mass of the cell culture media in the reservoir. The fluid amount sensor can be a volume sensor, such as an optical sensor, that can detect the volume of the cell culture media in the reservoir. In some examples, other types of sensors can be used to detect an amount of the cell culture media in the reservoir.

The fluid amount sensor can be in wired or wireless communication with the computing system of the automated cell culture system 100. For instance, when the amount of cell culture media in the reservoir 202 (e.g., used as a proxy for the amount of cell culture media in the fluidic circuit) falls below a threshold amount, the computing system of the automated cell culture system 100 can automatically control the pump 208a to pump fresh cell culture media into the fluidic circuit. The threshold amount can be a percentage of the capacity of the reservoir 202, e.g., about 80% of the capacity, about 60% of the capacity, about 50% of the capacity, about 40% of the capacity, or another amount. The threshold amount can be a volume, e.g., about 100 mL, about 200 mL, about 300 mL, about 400 mL, about 500 mL, or another amount. The threshold amount can be based on the phase of the cell culturing, as discussed below. The computing system can cause an alert to be output on a user interface, such as on the display 106, e.g., when the amount of cell culture media in the reservoir 202 falls below the threshold amount.

In some examples, the automated cell culture system 100 can include a fluid amount sensor 226, housed in or mounted on the reactor portion 104, to detect an amount, such as a mass or volume, of cell culture media in the fresh media source 206. The fluid amount sensor can be a mass sensor, such as a strain gauge, that can detect the mass of the cell culture media in the fresh media source. The fluid amount sensor can be a volume sensor, such as an optical sensor, that can detect the volume of the cell culture media in the fresh media source. In some examples, other types of sensors can be used to detect an amount of the cell culture media in the fresh media source. In some examples, the automated cell culture system 100 can include a fluid amount sensor, housed in or mounted on the reactor portion 104, to detect an amount, such as a mass or volume, of cell culture media in the waste destination.

The fluid amount sensor 226 can be in wired or wireless communication with the computing system of the automated cell culture system 100. For instance, when the amount of cell culture media in the fresh media source 206 falls below a threshold amount, the computing system of the automated cell culture system 100 can cause an alert to be output on a user interface, such as on the display 106, to alert the user that a new fresh media source may be necessary. The fluid amount sensor that detects the amount of cell culture media in the waste destination can also be wired or wireless communication with the computing system. For instance, when the amount of cell culture media in the waste destination exceeds a threshold amount, the computing system of the automated cell culture system 100 can cause an alert to be output on a user interface, such as on the display 106, to alert the user that the waste destination may need to be emptied or replaced.

In some examples, one or more of the detected parameters can be used by the computing system to determine a phase of the cell culturing, e.g., an initial, slow growth phase, in a rapid (e.g., exponential) growth phase, or in a plateau in which cell proliferation is reduced or ceases. For instance, the glucose or lactate levels in the cell culture media, the dissolved oxygen concentration in the cell culture media, the rate at which the amount of nutrients in the cell culture media in the fluidic circuit decreases, or other parameters can be indicative of the phase of the cell culturing.

The computing system of the automated cell culture system 100 can determine the phase of the cell culture process based on one or more of the detected parameters, or based on a change in one or more of the detected parameters over time. The computing system can control operation of one or more components responsive to the determined phase of the cell culture process. For instance, when cell culturing is in an initial phase, the computing system can automatically, without user input, control the pumps 212a, 212b to keep the volume of cell culture media in the fluidic circuit low, thereby enabling a high concentration of a growth factor in the cell culture media to be achieved. In the rapid growth phase, the computing system can automatically, without user input, control the pumps 212a, 212b to increase the volume of cell culture media in the fluidic circuit. The computing system can control the addition of cell culturing reagents, e.g., growth factors, based on the phase of the cell culturing. The computing system can control the operation of the heater 218 to maintain the cell culture vessel 200 at a target temperature that is specific to the phase of the cell culturing. The computing system can control the operation of one or more mass flow controllers or valves, or a combination of both, to provide carbon dioxide or nitrogen to the interior of the reactor portion to maintain a target carbon dioxide or oxygen concentration in the air specific to the phase of the cell culturing, or to maintain a target pH or dissolved oxygen concentration in the cell culture media specific to the phase of the cell culturing. The computing system can cause an alert to be output on a user interface, such as on the display 106, e.g., to indicate the determined phase of the cell culturing, to indicate that the cell culturing has reached a plateau, to alert the user to take an action (e.g., manual addition of a reagent such as growth factor, harvesting of cultured cells, or another action), to notify the user that an action (e.g. addition of a reagent such as growth factor, refresh of cell culture media, or another action) has been implemented automatically, or for other reasons.

Figure 3:
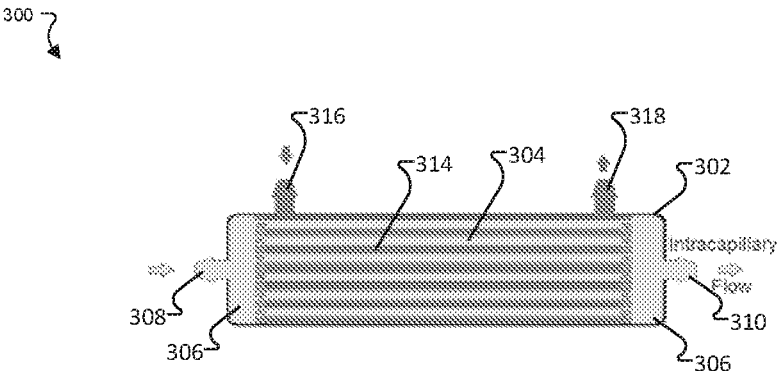
FIG. 3 is a diagram of a hollow tube cartridge.

Referring to FIG. 3, a hollow tube cartridge 300 is an example of a cell culture vessel for use with the automated cell culture system. The hollow tube cartridge 300 can be a sterile, self-contained environment, e.g., sterilized by gamma irradiation, and can be a disposable cartridge designed for a single use.

The hollow tube cartridge 300 includes an outer, cylindrical casing 302 defining an interior space. Multiple tubes, referred to as capillaries 304, are disposed in the interior space of the casing 302 such that the longitudinal axes of the capillaries 304 is substantially aligned with the longitudinal axis of the cartridge 300. The capillaries 304 can be formed of a material capable of supporting cell growth, such as a polymer, e.g., polysulfone. The material can be a porous material such that the walls of the capillaries are fenestrated, e.g., porous. The capillaries 304 are set in plugs 306 at each end of the casing 302 to seal the ends of the capillaries within the casing 302 such that an interior space of each capillary 304 (referred to as intra-capillary space) is fluidically connected to an inlet 308 and an outlet 310 of the cartridge 300. The inlet 308 and outlet 310 of the cartridge 300 can be connected to tubing of the fluidic circuit.

The space outside the capillaries 304 but within the interior of the casing 302 is referred to as extra-capillary space 314. Cell culturing occurs in the extra-capillary space 314. The extra-capillary space 314 is fluidically connected to an inlet fitting 316 and an outlet fitting 318, such as barb fittings that pierce the casing 302 of the cartridge 300. The fittings 316, 318 can be connected to tubing, e.g., for provision of cell culturing reagents such as cells, serum, growth factors, immunological stimulants such as cytokine, or other high molecular weight materials. Because the walls of the capillaries 304 are porous, nutrients can pass from the intra-capillary space into the extra-capillary space 314 to supply the culturing cells, and cell culturing waste products can pass from the extra-capillary space 314 to the intra-capillary space to be flushed out of the cartridge 300 by the flow of cell culture media through the fluidic circuit. The size of the pores can determine the size of the molecules that can pass between the intra-capillary space and the extra-capillary space 314. For instance, the pores can be sized to allow passage of molecules sized between about 10 kDa and about 0.2 μm, e.g., about 10 kDa, about 20 kDa, about 50 kDa, or about 0.1 μm.

The extra-capillary space 314, where cell culturing occurs, is space constrained. For instance, the extra-capillary space 314 can have a volume of between about 10 mL and about 100 mL, e.g., between about 10 mL and about 70 mL, between about 30 mL and about 70 mL, between about 50 mL and about 70 mL, between about 30 mL and about 50 mL, or another volume. The small volume in the extra-capillary space 314 enables enabling cell culturing reagents such as growth factor, serum, or other reagents to be present in relatively high concentrations, thus facilitating efficient cell culture. In some examples, the small volume in the extra-capillary space 314 also causes the cultured cells to be close together, facilitating inter-cellular communication that can improve cell culturing efficiency. In some examples, cell culture can also be accommodated in the intra-capillary space, with cell culturing reagents, such as high molecular weight nutrients constrained on the same side, e.g., when a relatively low overall cell yield can be acceptable, to help enhance inter-cellular communicated, or for other reasons.

Features of the cartridge, such as volume, capillary material, pore size, or other features, can be customizable based on the cells to be cultured. For instance, cartridge features can be selected to achieve target flow rates, gas exchange rates, nutrient and waste exchange rates, or other aspects of cell culture, e.g., to promote efficient expansion of viable cells.

The computing device of the automated cell culture system 100 can adjust the amount of cell culture media in the fluidic circuit depending on the phase of the cell culturing. For instance, a relatively low amount of cell culture media can be provided at the outset of cell culturing so that the concentration of cell culturing reagents such as growth factor in the extra-capillary space 314 of the hollow tube cartridge 300 can be high, facilitating cell growth. In a later phase of the cell culturing, the amount of cell culture media can be increased.

Referring to FIG. 4, in the fluidic circuit 400 of the automated cell culture system, the pump 204 pumps cell culture media from the reservoir 202 to the culture vessel 200 and back to the reservoir 202 to circulate cell culture media through the fluidic circuit 400. The reservoir 202 for cell culture media in the fluidic circuit 400 can be a bottle or other receptacle for cell culture media. For instance, the reservoir 202 can have a volume of about 500 mL. The reservoir 202 can be hermetically sealed and can have a vent to allow equilibration to atmospheric pressure. The vent can include an air filter 402, such as a 0.2 micron filter.

The reservoir 202 can be fluidically connected to the culture vessel 200 by tubing 404, such as silicone tubing, e.g., ¼" outer diameter silicone tubing. Features of the tubing, such as wall thickness, length, or other features, can be customizable based on the cells to be cultured. For instance, tubing features can be selected to achieve target flow rates, gas exchange rates, nutrient and waste exchange rates, or other aspects of cell culture, e.g., to promote efficient expansion of viable cells.

Cell culture media is pumped through the tubing of the fluidic circuit from the reservoir 202 to the culture vessel 200, and from the culture vessel 200 to the reservoir 202, by the pump 204. For instance, circulation of cell culture media through the fluidic circuit can circulate cell culture media through the intra-capillary space of the hollow fiber cartridge, delivering nutrients to the culturing cells and removing waste products from the cartridge. The pump 204 can be a peristaltic pump, such as a finger-type peristaltic pump, that enables continuous use of the same tubing for multiple days or multiple weeks, e.g., up to two weeks, up to one month, up to two months, up to three months, or for another amount of time.

The cell culture media pumped from the reservoir 202 passes through gas exchange tubing 408 prior to arriving at the culture vessel 200. The gas exchange tubing 408 can be made of a material sufficient to satisfy metabolic gas exchange parameters of the cultured cells. For instance, the gas exchange tubing 408 can be platinum cured silicone. One or more sensors can be disposed along the length of the tubing 404 between the reservoir 202 and the culture vessel 200, such as the colorimetric pH sensor 214 or sensors 410 including one or more of other pH sensors, a dissolved oxygen sensor, a glucose sensor, a lactate sensor, or other types of sensors.

Cell culture media can be pumped into the fluidic circuit 400 from the fresh media source 206 through input tubing 412 by the pump 208a, such as a peristaltic pump. Cell culture media can be pumped out of the fluidic circuit to a waste destination 416 through output tubing 418 by the pump 208b, such as a peristaltic pump. The process of pumping fresh cell culture media into the fluidic circuit 400 from the fresh media source 206 and pumping cell culture media out of the fluidic circuit 400 to the waste destination 416 is referred to as cell culture media exchange. The fluidic circuit 400 and the input and output tubing 412, 418 are arranged such that cell culture media exchange can be carried out substantially without disturbing the cells culturing in the culture vessel 200. For instance, valves 420, 422, 424, such as pinch valves, can be actuated to allow cell culture media exchange to occur substantially without disturbing the cells. For instance, the valve 420 can be opened and the valves 422, 424 can be closed during cell culture media exchange. In some examples, a portion of the culture vessel (e.g., the intra-capillary side of a hollow fiber cartridge) can be flushed with cell culture media at a lower flush rate during cell culture media exchange.

Other materials relevant to cell culture, such as cells, serum, growth factors, or other high molecular weight materials (referred to collectively as reagents), can be provided directly to the culture vessel 200 through input tubing 426. For instance, the input tubing can be fluidically connected to the extra-capillary side of a hollow fiber cartridge.

The fluidic circuit 400 can be a hermetically sealed fluidic circuit. To maintain the hermetic seal of the fluidic circuit 400, connections into and out of the fluidic circuit 400 can be one-way connections. For instance, an input connection to the input tubing 412 connected to the fresh media source 206 can be a one-way valve that enables fluid flow only into the fluidic circuit 400. An output connection to the output tubing 418 connected to the waste destination 416 can be a one-way valve that enables fluid flow only out from the fluidic circuit 400. An input connection to the input tubing 426 for input of reagents can be a one-way valve that enables flow of material only into the fluidic circuit 400. To maintain the hermetic seal of the fluidic circuit 400 even when changing the fresh media source 206, the waste destination 416, or a reagent source, the fresh media source 206, waste destination 416, and reagent source can be connected to the respective input and output tubing 412, 418, 426 by a heat welding connection 434, 436, 438 through thermoplastic tubing, such as polyvinyl chloride (PVC) tubing, enabling connections to be made without exposure to ambient air.

In some examples, cell culture media exchange can be carried out under automated, computer control responsive to a detected parameter of the cell culture media, such as pH, dissolved oxygen concentration, amount of cell culture media in the reservoir 202, or another parameter. For instance, if the pH of the cell culture media or the amount of cell culture media in the reservoir falls below a threshold pH or a threshold amount, respectively, the pump 208a can be controlled to pump additional cell culture media into the fluidic circuit 400 from the fresh media source 206. In some examples, cell culture media exchange can be carried out under automated, computer control responsive to the determined phase of cell culturing. For instance, the threshold amount of cell culture media in the reservoir can depend on the phase of cell culturing. If the amount of cell culture media in the reservoir during a particular phase of cell culturing falls below the threshold amount for that phase, the pump 208a can be controlled to pump additional cell culture media into the fluidic circuit.

The flow rate of cell culture media circulating in the fluidic circuit 400 can be controlled by the computer system, e.g., through control of the operation of the pump 204. For instance, the target flow rate of cell culture media in the fluidic circuit 400 can depend on the phase of cell culturing, e.g., in early phases, the flow rate can be slow so as not to disturb the cells, and in later phases such as rapid growth phases, the flow rate can be higher to efficiently provide nutrients to the culturing cells and remove waste from the cell culture vessel 200. The pump 204 can be controlled automatically and without user input by the computer system responsive to the phase of cell culturing, e.g., as determined by the computer system.

Figure 5:
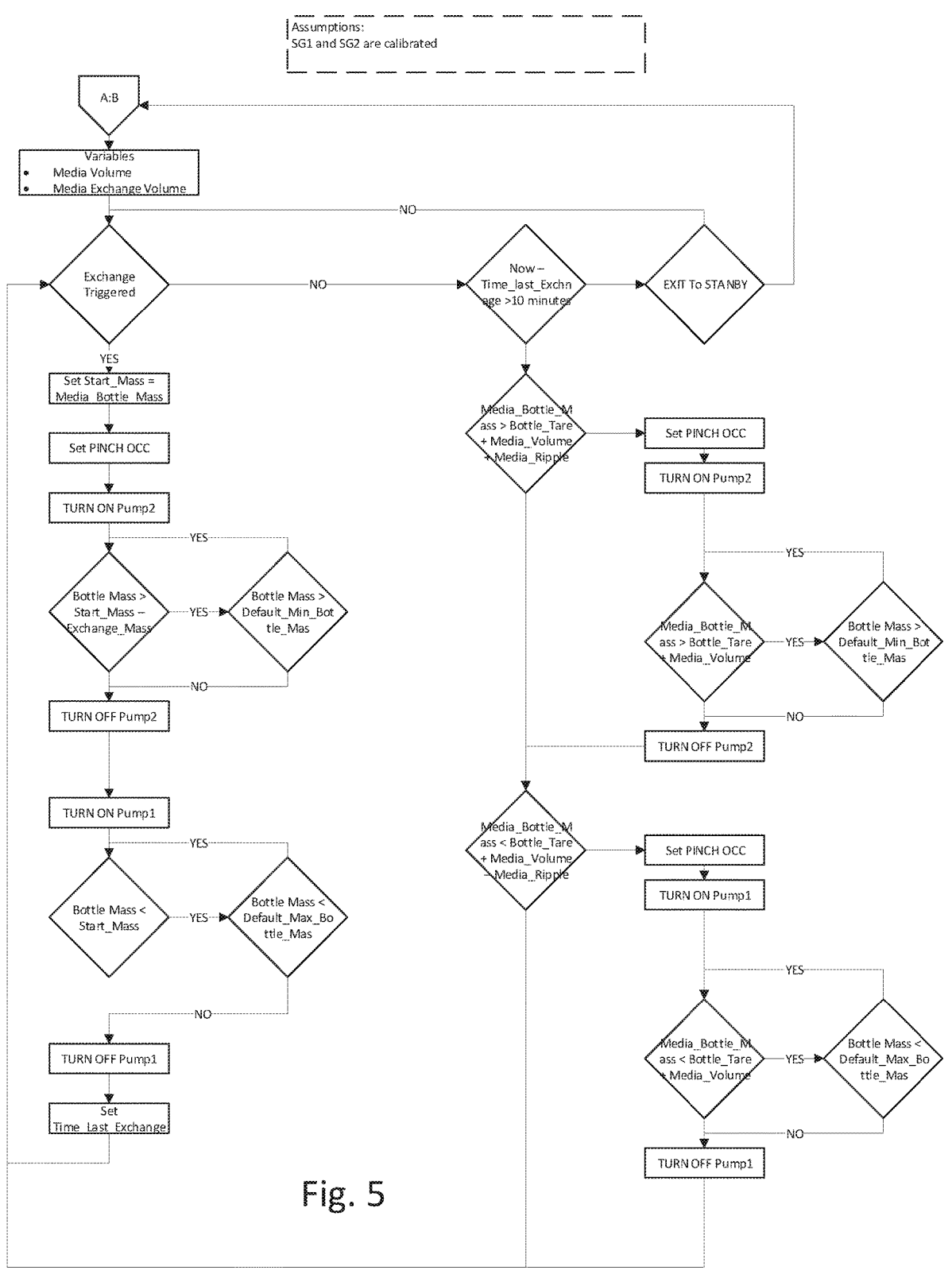
FIGS. 5 and 6 are flow charts.

Referring to FIG. 5, in an example of a cell culture media exchange process, a media exchange is triggered. Prior to initiating the exchange, the weight of the fresh media source is checked to confirm that there is sufficient cell culture media in the fresh media source to support the exchange. If there is not sufficient cell culture media in the fresh media source, an alert can be triggered, e.g., for display on the user interface. The available capacity of the waste destination can also be checked to confirm that the waste destination has sufficient capacity to receive the media from the exchange. For instance, the accumulated amount of media previously transferred to the waste destination is compared to the capacity of the waste destination. If there is not sufficient available capacity in the waste destination, an alert can be triggered.

Referring also to FIG. 4, during the exchange, the pump 204 in the fluidic circuit continues to circulate cell culture media through the fluidic circuit. The valves 420, 422, 424 are set to open, closed, and closed, respectively. The waste destination pump 208b is activated until the drop in the amount (e.g., weight or volume) of cell culture media in the reservoir 202 meets or exceeds the amount of cell culture media to be exchanged. The source pump 208a is then activated until the rise in the amount of cell culture media in the reservoir 202 meets or exceeds the amount of cell culture media to be exchanged. The amount of media exchanged can be logged in a capacity log of the waste destination.

In some examples, the media exchange process can occur under timed control. Each exchange operation can be timed under control of a logic timer, and a failure to complete an operation in the programmed time for that operation can give rise to an alert.

Figure 6:
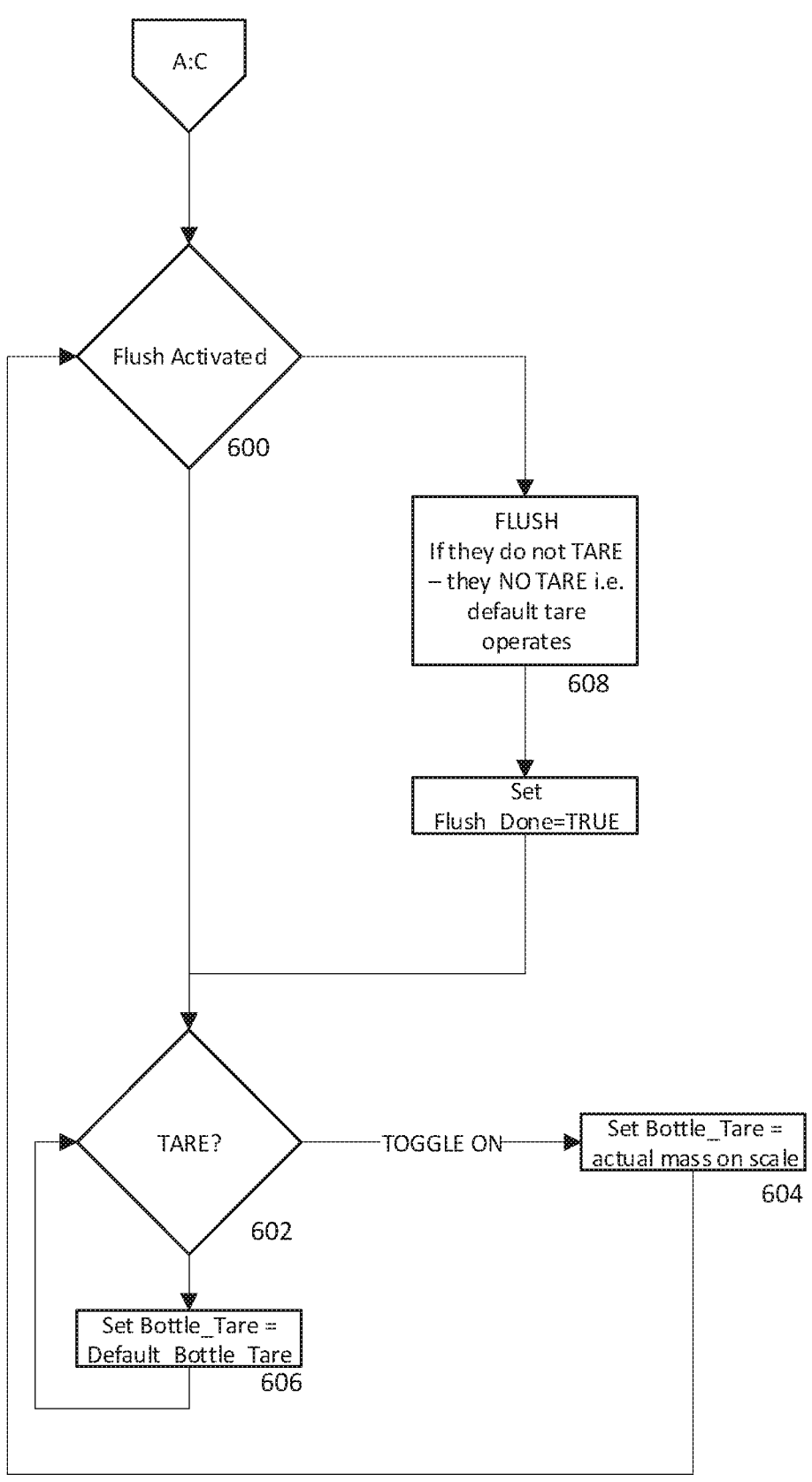

Referring to FIG. 6, in an example process, a culture vessel including a hollow fiber cartridge can be flushed, e.g., to elute impurities or contaminants such as manufacturing chemicals from the hollow fiber cartridge. The flushing process can be automated under computer control, and can be carried out at flow rates and for a duration that can be specified by a user, e.g., by input through a user interface. The user can also input instructions indicative of the fluid or fluids to be used in the flushing process.

The flushing process is activated (600), e.g., responsive to user instructions to activate the flushing process. At the start of the flushing process, the weight of the empty reservoir (e.g., the reservoir 202 in FIG. 2) can be tared (602). For instance, the user can be prompted to select whether to tare the empty reservoir. If the reservoir is tared, the weight of the empty reservoir, e.g., stored in memory, in a table of a database, or otherwise, is set to the mass of the empty reservoir as measured (604). If the reservoir is not tared, the weight of the empty reservoir is set to a default value (606). In some examples, the user can provide a default value for the weight of the empty reservoir. In some examples, the user can provide an identifier of the type of the reservoir and the weight of the empty reservoir can be set to a default value for the type of the reservoir.

The flush process is activated (600) after the weight of the empty reservoir is set. Referring also to FIG. 4, the flush proceeds (608) by filling the culture vessel 200, such as a hollow fiber cartridge, using the pump 208a to pump fresh cell culture media from the fresh media source 206 into the reservoir 202. The pump 204 circulates cell culture media from the reservoir 202 into the culture vessel 200. When the culture vessel 200 is filled with cell culture media, the pump 204 continues running to circulate cell culture media through the fluidic circuit 400. During the initial portion of the flush, all valves 420, 422, 424 are open.

When the reservoir 202 reaches its target amount of cell culture media, the pump 208a stops pumping cell culture media from the fresh media source 206. The valves 420, 422, 424 are set to closed, closed, and open, respectively, to fill the extra-capillary space of the hollow fiber cartridge 200. After an amount of time, e.g., 5 minutes, the valves 420, 422, 424 are set to closed, open, and closed, respectively, to purge air bubbles from the hollow fiber cartridge 200. After an amount of time, e.g., 5 minutes, the valves 420, 422, 424 are set to open, closed, and closed, respectively, for cartridge balancing.

The first balance of the hollow fiber cartridge 200 is maintained for a preset duration before cell culture media exchange is triggered. Upon completion of the preset duration, the pump 208b is activated to transfer cell culture media from the reservoir 202 to the waste destination 416. A second balance of the hollow fiber cartridge 200 is then carried out, with a duration twice that of the first balance.

The amount of cell culture media exchanged (e.g., the weight or volume) and the capacity of the waste destination 416 can be monitored during the balancing process, e.g., to help ensure that the reservoir 202 is not breached due to overfilling of the waste destination 416, and to help ensure that the reservoir 202 itself is not overfilled.

Figure 7:
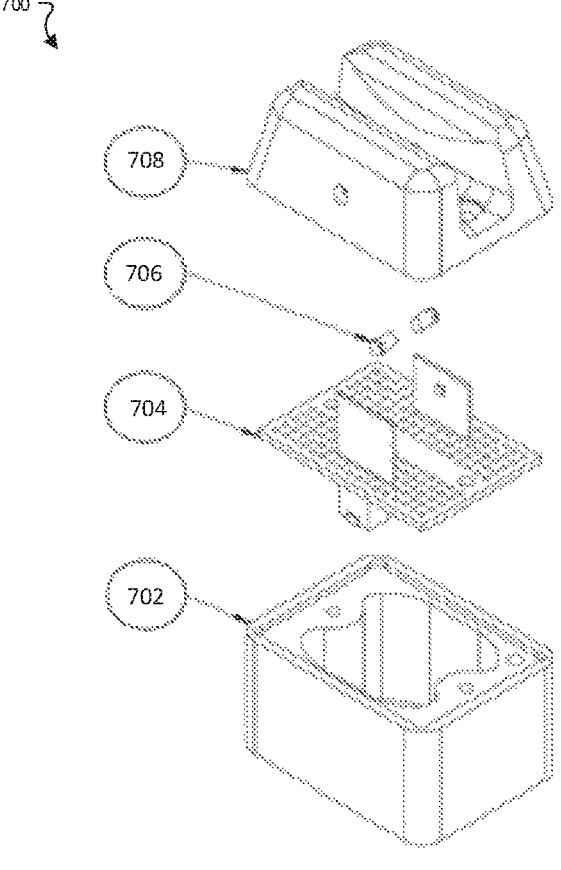
FIG. 7 is a diagram of a pH sensor.

Referring to FIG. 7, an example pH colorimetric sensor 700 detects pH of fluid, such as the cell culture media in the fluidic circuit of the automated cell culture system, based on the hue of the fluid. The pH colorimetric sensor 700 includes a sensor holder 702 that holds a color sensor assembly 704 and a light pipe 706. A clamp 708 clamps the pH colorimetric sensor 700 to tubing (e.g., the tubing 404 of the fluidic circuit 400; see FIG. 4) such that the tubing is disposed between two portions of the light pipe 706. The light pipe and color sensor assembly 704 detect the hue of cell culture media containing a pH sensitive dye, such as phenol red, in the tubing of the fluidic circuit. The detected hue is provided to the computing system of the automated cell culture system. The computing system compares the measured hue of the fluid against a reference source, e.g. a four-term polynomial conversion function, a deterministic equation, or a data lookup table of sufficient resolution, to determine a value for the pH of the fluid.

Figure 8:
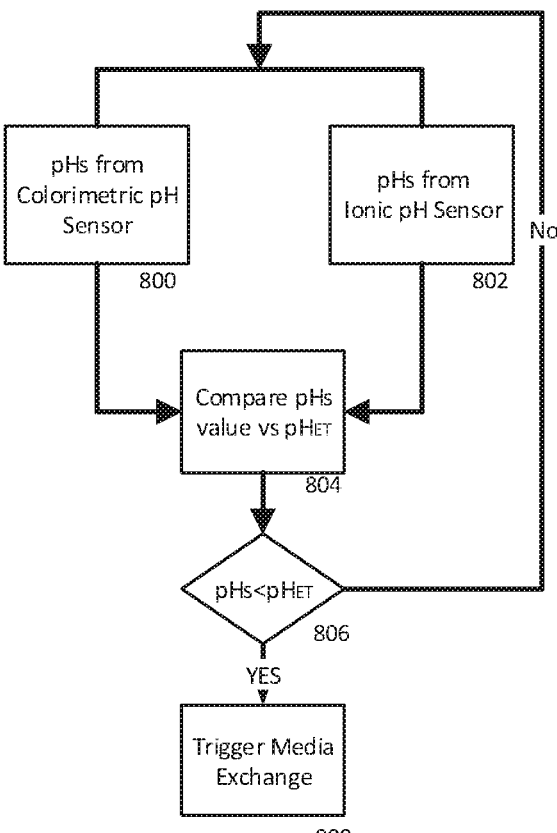
FIG. 8 is a flow chart.

Referring to FIG. 8, cell culture media in the automated cell culture system can be exchanged based on the pH of the cell culture media in the fluidic circuit. For instance, the pH of the cell culture media decreases as cell culture proceeds; to keep the pH of the cell culture media within a preset range, or above a preset threshold value, the cell culture media can be exchanged based on the pH of the cell culture media. In an example process for exchange of cell culture media, the pH of the cell culture media is detected by colorimetric pH sensor (e.g., the sensor 700 of FIG. 7) (800). The pH of the cell culture media is detected by an ionic pH sensor (802). In some examples, the pH of the cell culture media can be detected by another type of pH sensor. In some examples, the pH of the cell culture media is detected by only a single pH sensor. One or more of the detected pH values are compared to a threshold pH value (804), such as a default threshold value or a threshold value set by a user of the automated cell culture system. In some examples, a value determined based on multiple detected pH values, such as an average pH value, is compared to the threshold pH value. If the detected pH value of the cell culture media is less than (or less than or equal to) the threshold pH value (806), an exchange of cell culture media is initiated (808), e.g., as described above with reference to FIG. 5. If the detected pH value of the cell culture media is greater than (or greater than or equal to) the threshold pH value (806), no cell culture media exchange is initiated and the one or more pH sensors and the local or remote computing system continue to monitor the pH of the cell culture fluid. In some examples, the pH monitoring process is a continuous, real-time process. In some examples, pH monitoring occurs at regular intervals, such as every 1 minute, 2 minutes, 5 minutes, 10 minutes, 15 minutes, 30 minutes, 1 hour, or at another interval.

Figure 9:
FIG. 9 is a diagram of a temperature control subsystem.
Figure 9:
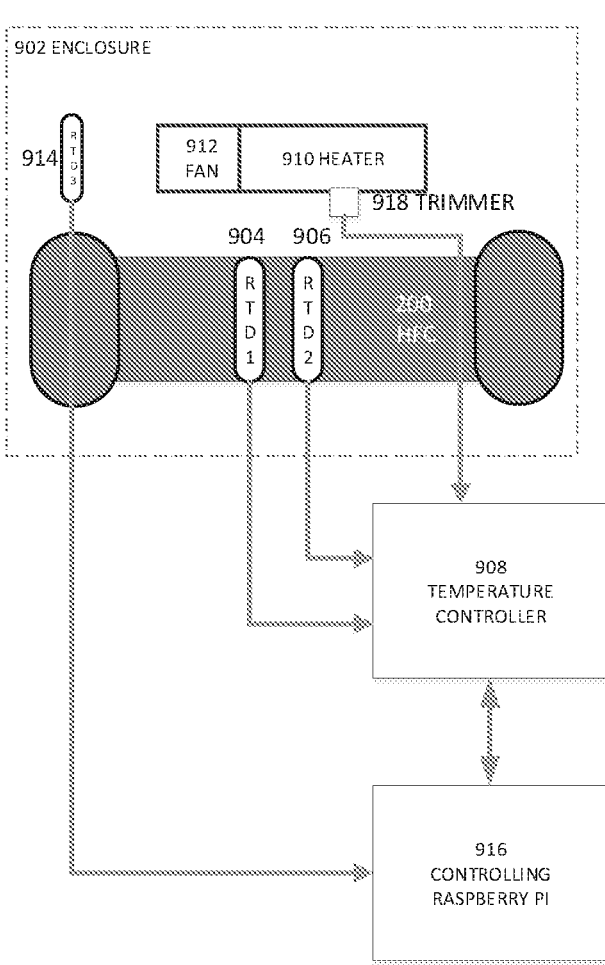

Referring to FIG. 9, an example of a thermal subsystem 900 monitors and controls the temperature in the interior of the reactor portion of the automated cell culture system. The culture vessel, such as a hollow fiber cartridge, can be housed within a cover 902, such as a double layer metal cover, e.g., an aluminum cover. For instance, the cover 902 can be the cover 105 of the reactor portion of the automated cell culture system (see FIG. 1), or can be another cover. The cover can be thermally insulating to help maintain the temperature of the environment within at a target temperature for cell culture. The cover can be partially or completely impermeable to one or more gases, such as one or more of carbon dioxide, oxygen, or other gases relevant to cell culture, to help maintain target gas concentrations in the cell culture media within the culture vessel. The cover can be hinged to provide access to the culture vessel therein.

The thermal subsystem 900 includes temperature sensors 904, 906 that are connected to the culture vessel 200. For instance, the temperature sensors 904, 906 can form part of the temperature sensor 216 (see FIG. 2). The temperature sensors 904, 906 can be mounted to the exterior of the culture vessel 200 by a mounting device, such as a molded silicone pedestal. The temperature sensors 904, 906 are devices that can detect the temperature of the culture vessel, or that provide an output from which the temperature of the environment can be determined. For simplicity, we refer to both of these cases as the temperature sensors detecting the temperature. For instance, the temperature sensors can be thermometers, thermistors, thermocouples, semiconductor-based sensors, or other types of temperature sensors.

In some examples, a single temperature sensor can be used; in some examples, more than two temperature sensors can be used. In some examples, multiple temperature sensors can provide redundancy in the event of a failure of one of the temperature sensors. In some examples, a particular one of the temperature sensors (e.g., the sensor 904) can be designated as a primary temperature sensor and the computing system of the automated cell culture system can receive temperature readings from that primary temperature sensor. If the computing system of the automated cell culture system detects a failure in the primary temperature sensor, the computing system can switch to receive temperature readings from another one of the temperature sensors (e.g., the sensor 906). In some examples, the computing system can cause an alert to be output to alert a user of the sensor failure, such as an audible alert, a text or graphical alert on the user interface of the automated cell culture system or on a user interface of a remote computing device, an alert light, or another type of alert. In some examples, the computing system can cause an alert to be output for another reason, e.g., even if not failure is detected, such as if two temperature sensors are in disagreement, e.g., if the detected temperatures are more than a threshold percentage different, e.g., more than 2% different, more than 5% different, more than 10% different, or another amount.

The thermal subsystem 900 includes a temperature controller 908, such as a proportional-integral-derivative controller (PID) controller, that receives signals from the temperature sensors 904, 906 and controls the operation of one or more of a heater 910 and a fan 912 responsive to the signals received from the temperature sensors 904, 906, e.g., in a closed loop feedback system, to control the temperature in the culture vessel. For instance, the temperature controller 908 can control the temperature of the culture vessel to be a preset temperature, such as a default temperature or a temperature input by a user through the user interface of the automated cell culture system or through a user interface of a remote computing device. In some examples, the temperature controller 908 can control the heater 910 using pulse width modulation to provide a high level of safe heat output from the heater 910 given the difference between the measured temperature and the preset temperature. The fan 912 can be positioned to provide air flow over heating elements of the heater 910, to provide air flow within the cover 902, or both. In some examples, the fan 912 can be operable independently of the heater, e.g., to provide cooling functionality, to maintain air mixing inside the cover 902, or to maintain air flow feeding onto the sensors, such as gas sensors 156, 162 and a gas temperature sensor 914 (see below). In some examples, the heater 910 can include an emergency cutoff sensor 918, such as a trimmer, that can shut off the heater 910 responsive to detecting a fault, e.g., a catastrophic fault, in the heater 910, thus helping to prevent ignition of components of the automated cell culture system and to reduce the risk of burns to a user of the system.

The temperature controller 908 can be a discrete component of the automated cell culture system, as shown in FIG. 9, or can be a module of a computing system 916 of the automated cell culture system. In some examples, e.g., depending on the type of the temperature sensors 904, 906, the temperature controller 908 can receive and buffer signals from the temperature sensors 904, 906. When the temperature controller 908 is a discrete component, the temperature controller 908 can send signals to the computing system 916 of the automated cell culture system indicative of the temperature detected by the temperature sensors 904, 906. The computing system 916 can cause display of information indicative of the temperature on a user interface of the automated cell culture system or on a user interface of a remote computing system. The computing system 916 can process the received signals to determine whether the detected temperature is indicative of an alarm condition, e.g., whether the detected temperature is above an upper threshold temperature, below a lower threshold temperature, or otherwise indicative of an alarm condition. The computing system can cause an alert to be output to alert a user of the alarm condition, such as an audible alert, a text or graphical alert on the user interface of the automated cell culture system or on a user interface of a remote computing device, an alert light, or another type of alert.

In some examples, the thermal subsystem 900 can include a temperature sensor 914 that is mounted in proximity to the fan 912, such as on the input side of the fan 912, to monitor the temperature of the circulating air in the culture vessel inside the cover 902. The signal from the temperature sensor 914 can be provided to the temperature controller 908 or (as shown in the example of FIG. 9) directly to the computing system 916 of the automated cell culture system. The computing system can control operation of the heater 910, the fan 912, or both, based on the temperature detected by the temperature sensor 914. For instance, the computing system 916 can send a signal to the heater 910 causing the heater 910 to turn off when the temperature detected by the temperature sensor 914 exceeds a first threshold temperature, e.g., 45° C., 46° C., 48° C., 50° C., or another threshold temperature, to avoid overheating of the environment in the interior of the cover 902. The computing system 916 can send a signal to the heater 910 cause the heater 910 to resume when the temperature detected by the temperature sensor 914 falls below a second threshold temperature, e.g., 40° C., 42° C., 43° C., 45° C., or another threshold temperature. In some examples, the first and second threshold temperatures can be the same.

Figure 10:
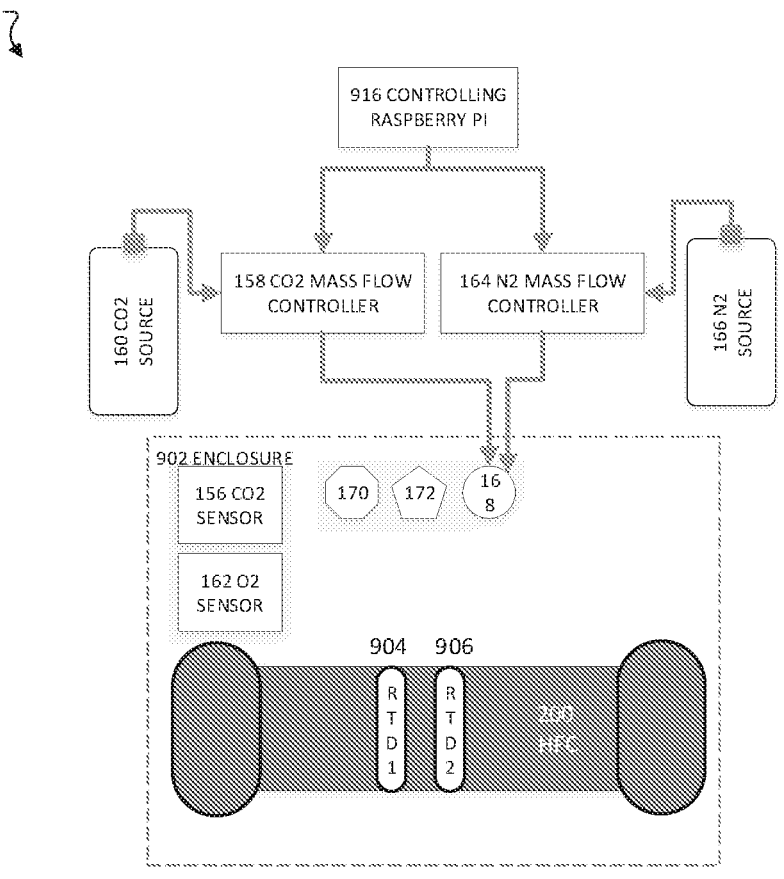
FIG. 10 is a diagram of a gas control subsystem.

Referring to FIG. 10, an example of a gas subsystem 150 monitors and controls the concentration of one or more gases in the air in the interior of the reactor portion 104 of the automated cell culture system, e.g., inside the cover 902. For instance, the gas subsystem 150 can monitor and control the concentration of carbon dioxide, which enables the cell culture media to provide a buffering function. In some examples, carbon dioxide can be controlled to a partial pressure of between about 0% and about 5%, e.g., between about 0.04% and about 6%. The gas subsystem 150 can monitor and control the concentration of oxygen ($O_2$), which can affect oxidative stress during cell culture and impact the growth and function of cultured cells. In some examples, oxygen can be controlled to a partial pressure of between about 0% and about 25%, e.g., between about 0% and about 21%, by displacement with nitrogen gas. The gas subsystem 150 can monitor and control the concentration of other gases in addition to or instead of carbon dioxide and oxygen.

A carbon dioxide sensor 156 detects the concentration of carbon dioxide inside the cover 902. The computing system 916 of the automated cell culture system, or a remote computing system, receives signals from the carbon dioxide sensor 156 and controls operation of a carbon dioxide mass flow controller 158 responsive to the received signals to maintain the concentration of carbon dioxide within a preset range. For instance, the computing system 916 can control the mass flow controller 158 to provide a flow of carbon dioxide from a carbon dioxide source 160 when the concentration of carbon dioxide falls below a threshold level.

An oxygen sensor 162 detects the concentration of oxygen inside the cover 902. The computing system 916, or a remote computing system, receives signals from the oxygen sensor 162 and controls operation of a nitrogen mass flow controller 164 responsive to the received signals to maintain the concentration of oxygen within a preset range. By increasing the concentration of nitrogen in the cover 902, the concentration of oxygen can be decreased. For instance, the computing system 916 can control the mass flow controller 164 to provide a flow of nitrogen gas ($N_2$) from a nitrogen gas source 166 when the concentration of oxygen rises above a threshold level. In some examples, $O_2$ enriched gas can be provided in the cover 902 to satisfy a target oxygen concentration when the ambient atmosphere cannot compensate for gas consumption, e.g., $O_2$ consumption, for instance due to excess biomass in the cell culture. For instance, a proportional-integral-derivative controller (PID controller) can be used to control the oxygen concentration.

Carbon dioxide, nitrogen, or other gases can be provided into the interior of the cover 902 through an outlet 168. One or more purge valves 170, 172 can allow for air to be purged into or out of the interior of the cover 902, e.g., if the concentration of carbon dioxide or oxygen deviate substantially from the preset ranges. In some examples, the computing system can cause an alert to be output to alert a user that a gas concentration is outside of a preset range, such as an audible alert, a text or graphical alert on the user interface of the automated cell culture system or on a user interface of a remote computing device, an alert light, or another type of alert.

Figure 11:
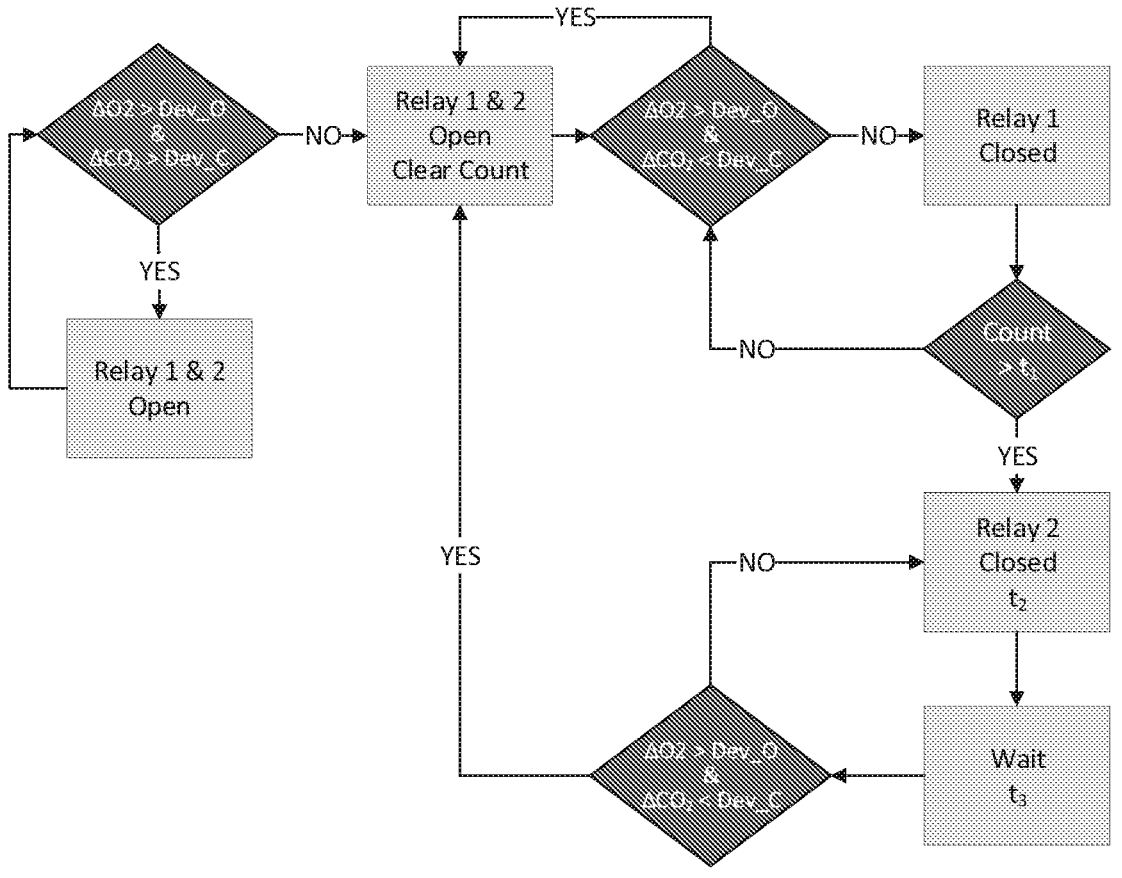
FIG. 11 is a flow chart.

Referring also to FIG. 11, in some examples, $CO_2$, $N_2$, or other gases are overdosed compared to the target concentration in the cover 902. The computing system computes a deviation ΔO2 between the level of oxygen measured in the atmosphere of the cell culture assembly and a target level of oxygen. The computing system also computes a deviation ΔCO2 between the level of carbon dioxide measured in the atmosphere of the cell culture assembly and a target level of carbon dioxide. If (1) the level of oxygen is higher than the target level of oxygen or the level of carbon dioxide is lower than the target level of carbon dioxide; and (2) the deviation ΔO2 exceeds a threshold deviation (Dev_O) for the oxygen level or the deviation ΔCO2 exceeds a threshold deviation (Dev_C) for the carbon dioxide level, a relay is closed to open the air valve 172. If the deviation of carbon dioxide or oxygen still exceeds the threshold deviation, a second relay is closed to open the air valve 170 and an air fan is triggered. The second relay can be opened and closed multiple times to open the air valve 170 and trigger the fan until neither deviation exceeds the threshold deviation.

In some examples, the culture vessel 200 can be mounted on a rotational mount. The rotational mount enables the culture vessel 200 to be rotated about one or more axes during the culturing cycle. Such rotational changes in orientation of the culture vessel 200 over the course of the culturing cycle can facilitate redistribution of cells, preventing formation of clumps of cells which can adversely affect cell growth and health.

Figure 12:
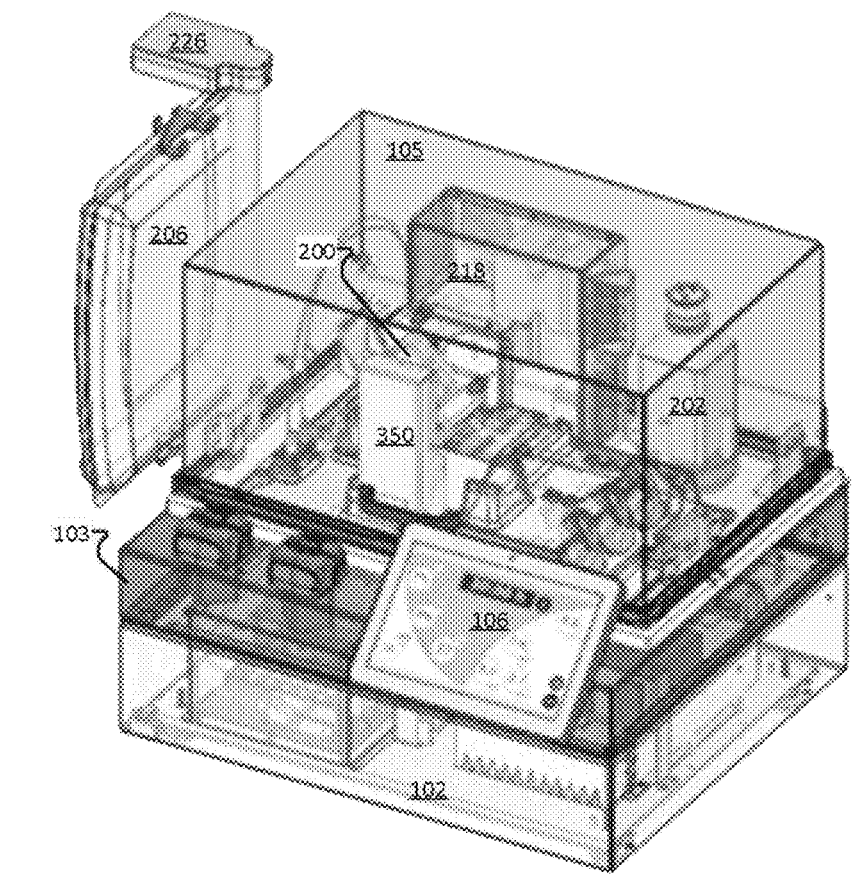
FIG. 12 is a diagram of a cell culture system.

Referring to FIG. 12, a rotational mount 350 can be incorporated into the automated cell culture system 100 in place of a stationary holder for the culture vessel 200.

Figures 13A, 13B, 13C:
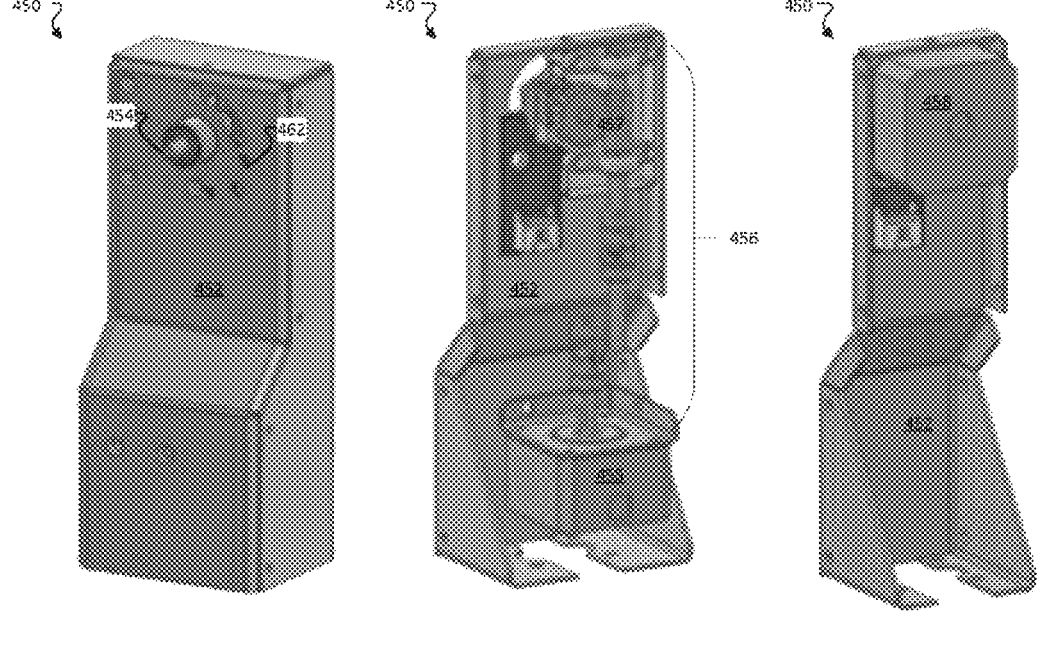
FIGS. 13A-13C are diagrams of a rotational mount.

Referring to FIGS. 13A-13C, an example rotational mount 450 includes a housing 452 having a mount 454 on which the culture vessel can be mounted. A mechanical rotation mechanism 456 can be housed within the housing 452. In some examples, the rotation mechanism can include a motor 455 coupled to a gear train 457, an arm linkage mechanism, or another component for transfer of rotational motion from the motor to the culture vessel 200.

Figures 14A, 14B, 14C:
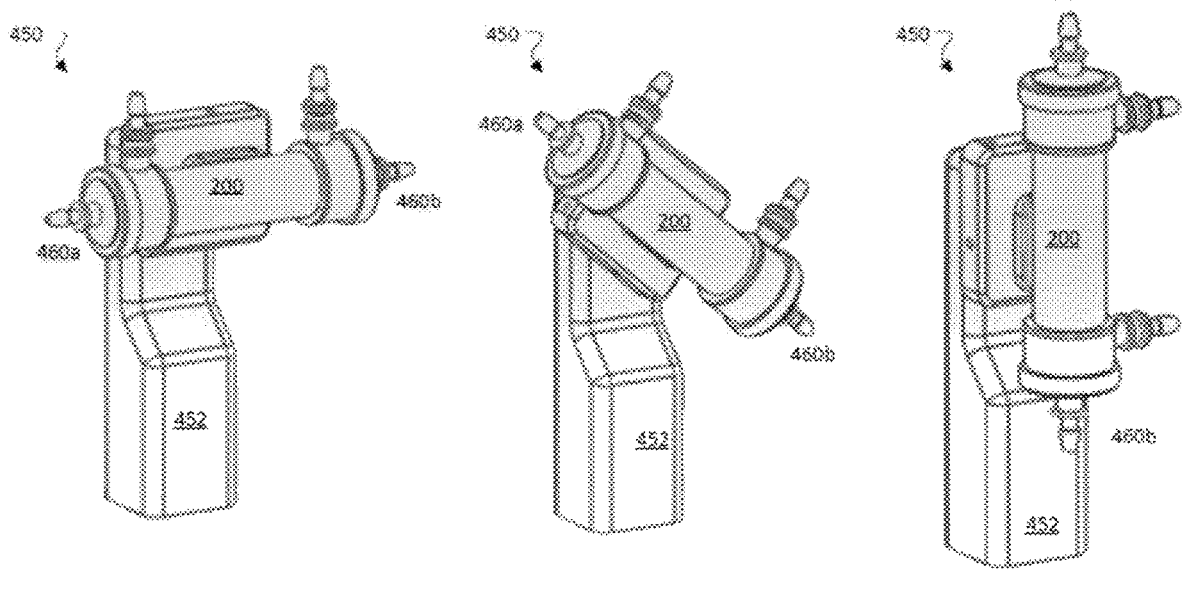
FIGS. 14A-14C are diagrams of a rotational mount.

Referring also to FIGS. 14A-14C, the culture vessel 200 is affixed to the mount 454 of the rotational mount 450 by a pedestal 458. The pedestal 458 can incorporate the temperature sensor 216 for sensing the temperature of the culture vessel 200.

The rotational mount 450 enables rotation of the culture vessel 200 end-over-end around an axis defined through the culture vessel. The axis can be defined through the center of the culture vessel or can be offset from the center of the culture vessel. In the examples of FIGS. 14A-14C, a rotation of 90° is shown, such that the culture vessel 200 is rotated from a horizontal orientation (FIG. 14A) to a vertical orientation (FIG. 14C). Further rotation can return the culture vessel 200 to a horizontal, but reversed, orientation, e.g., such that in an initial position a first end 460a of the culture vessel 200 is positioned on the left side of the rotational mount 450 and a second end 460b of the culture vessel 200 is positioned on the right side of the rotational mount 450; and in a final position the first end 460a is positioned on the right side and the second end 460b is positioned on the left side. This significant change in orientation can promote cell movement over, along, and around the hollow fiber bundle of the culture vessel 200, facilitating more proximal access to the nutrient mixture in the interior of the culture vessel 200 (e.g., the extra-capillary space 314, as shown in FIG. 3), while also facilitating redistribution of the cell population to a less dense distribution. In some examples, further rotation can be possible, e.g., a rotation of up to 270° or up to 360°.

Referring again to 13A and 13B, in some examples, a sensor 462, such as an optical sensor, can detect the rotational position of the culture vessel 200, e.g., to enable the rotation to be stopped at a maximum rotation. For instance, the sensor 462 can detect the position of the pedestal 458, e.g., detect whether a corner of the pylon has passed in front of the sensor 462, as a proxy for the rotational position of the culture vessel 200. In some examples (not shown), rotation of the culture vessel 200 can be stopped by a mechanical feature, such as a barrier that prevents rotation past a certain point.

Figures 15A, 15B:
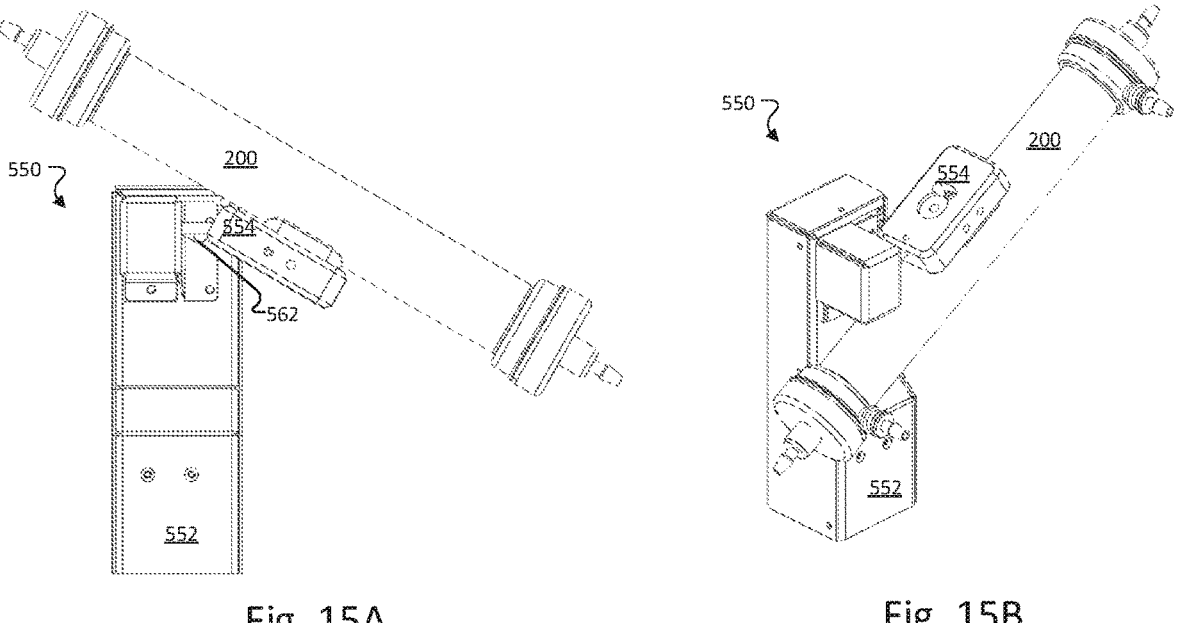
FIGS. 15A-15C are diagrams of a rotational mount.
Figure 15C:
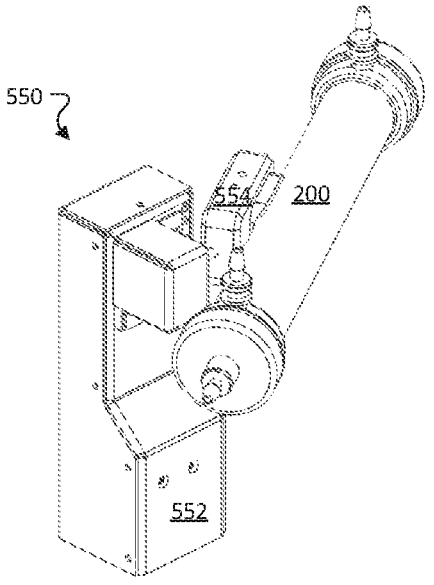

Referring to FIGS. 15A-15C, an example rotational mount 550 enables rotation of the culture vessel 200 about two separate axes. The rotational mount 550 includes a housing 552 having a mount 554 on which the culture vessel 200 can be mounted. A mechanical rotation mechanism (not shown) is housed within the housing 552 and enables rotation of the culture vessel 200 about two axes. As shown in FIGS. 15A-15C, the rotational mount 550 enables the culture vessel 200 to be rotated around an axis defined through the center of the culture vessel 200 and rotated (e.g., twisted) around the long axis of the culture vessel 200. In some examples, the mechanical rotation mechanism of the rotational mount 550 can be configured to enable rotation about a different axis. In some examples, the mechanical rotation mechanism can rotate the culture vessel 200 about both axes in a single movement. In some examples, the rotation of the culture vessel 200 about one axis can be independent of the rotation about the other axis. The amount of rotation around each axis can be different. For instance, the rotational mount 550 can enable an end-over-end rotation of the culture vessel 200 of ±180° and a twisting rotation of ±30°.

In some examples, a sensor 562, such as an optical sensor, can detect the rotational position of the culture vessel 200 such that the rotation can be stopped, e.g., when the culture vessel reaches a maximum rotation.

In some examples, operation of the rotational mount (e.g., 450 or 550) can be controlled manually, e.g., by a knob, lever, or other mechanism operable by a user of the cell culture system. In some examples, operation of the rotational mount can be controlled by the computing device that controls the cell culture system. For instance, the rotational mount can be controlled to rotate the culture vessel by a prescribed amount on a prescribed schedule. In some examples, the rotation can be triggered by a sensed characteristic of the cells in the culture vessel. The sensed characteristic can include a density of cells in the culture vessel, a consumption rate of glucose, an accumulation of lactate, an index that is based on a combination of characteristics such as the consumption rate of glucose and the accumulation of lactate, or another sensed characteristic. For instance, an optical sensor, such as a still or video camera, can capture images of an interior of the culture vessel, and image analysis can indicate a density of cells in the culture vessel. When the density of cells reaches a threshold density, rotation can be triggered.

In some examples, a temperature control system can be provided to maintain the temperature of the fresh media source at a target temperature. For instance, by storing the fresh media source at a low temperature, such as a temperature below room temperature, the lifetime of the fresh media source can be prolonged.

Figure 16:
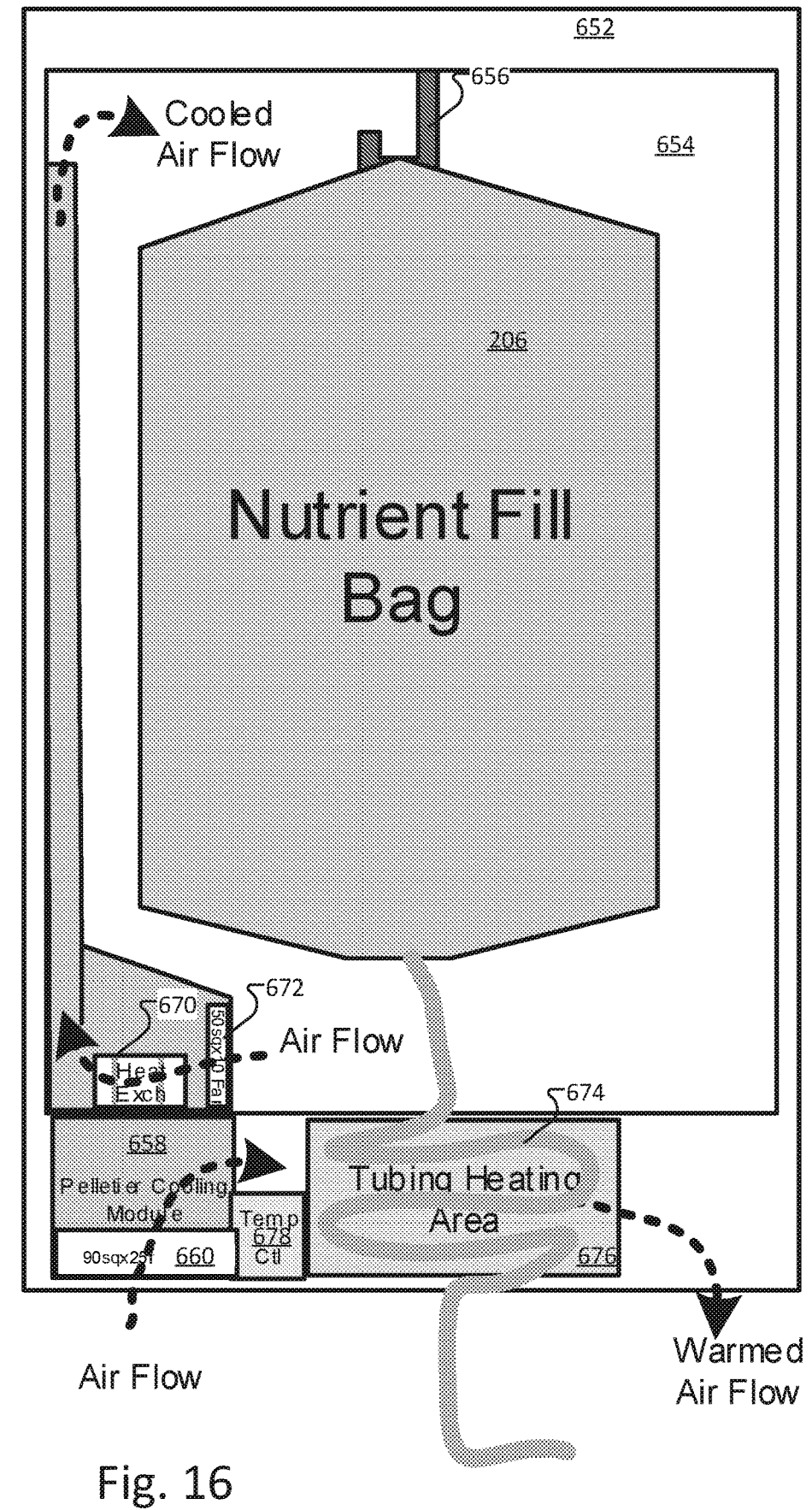
FIG. 16 is a diagram of a temperature control system.
Figure 17A:
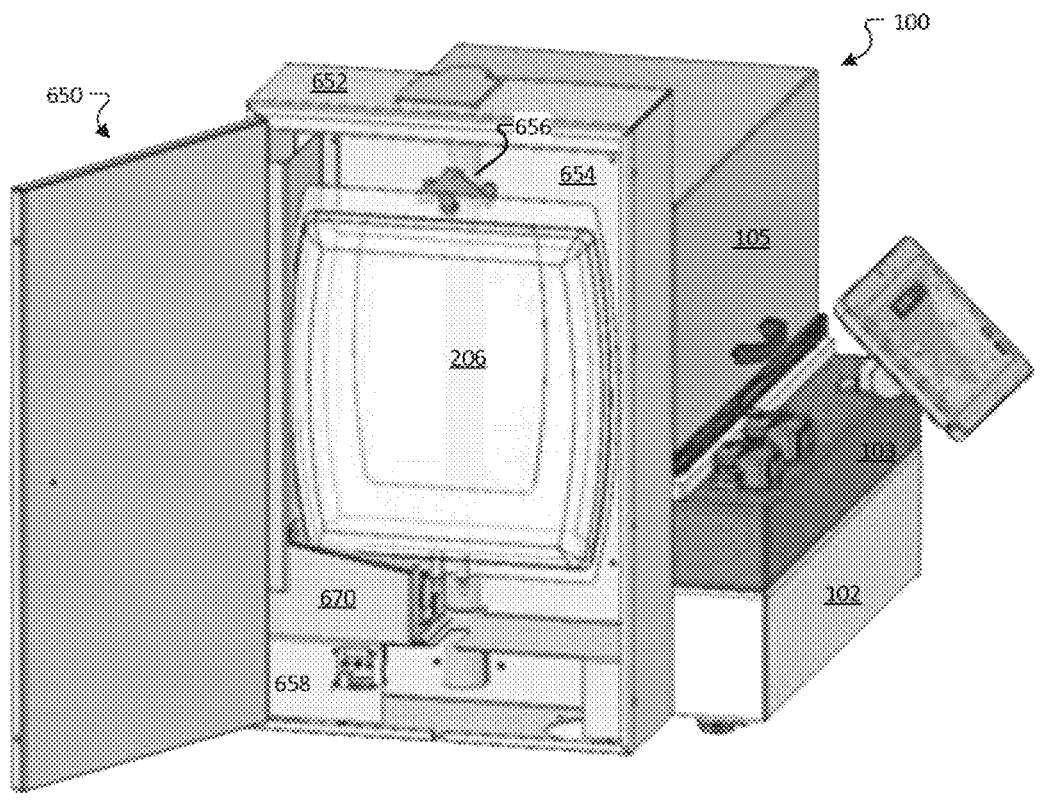
FIGS. 17A and 17B are diagrams of a temperature control system.
Figure 17B:
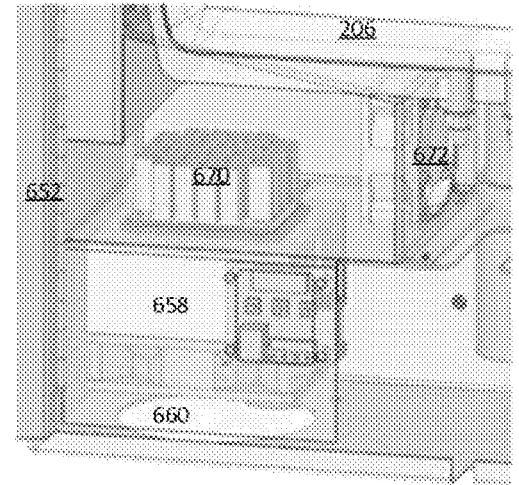

Referring to FIGS. 16 and 17A-17B, an example temperature control system 650 includes a housing 652, with the fresh media source 206 housed in an interior space 654 of the housing. The housing 652 can be, for instance, an insulating housing. A fluid amount sensor 656, such as a strain gauge or a volume sensor, can be mounted on or housed within the housing 652, to detect an amount, such as a mass or volume, of cell culture media in the fresh media source 206.

A temperature controlling module 658, such as a thermoelectric cooling module, e.g., a Peltier cooling module, generates an output for controlling the temperature of the interior space 654 of the housing. The output can be a cooling output or a warming output. For instance, warm air from the cell culture system (e.g., air warmed due to waste heat from the components of the cell culture system) can be flowed into the temperature controlling module 658 by a fan 660, and the temperature controlling module 658 can generate an output by thermoelectric cooling. Air from the interior space 654 is flowed through a heat exchanger 670, e.g., by a fan 672, such that the cooling output from the temperature controlling module 658 cools the air flow. The cooled air flow is output back into the interior space 654 to maintain the fresh media source 206 at the target temperature. A similar, but opposite, approach can generate a warming output.

In some examples, the cell culture media from the fresh media source 206 can be warmed prior to its introduction into the fluidic circuit of the cell culture system. A warming flow path 674 can be provided at the output of the fresh media source 206. The warming flow path 674 can pass through a warming area 676, e.g., an area heated by waste heat from the temperature controlling module 658 (as shown) or heated by a separate heating element. In some examples, the warming flow path 674 can include a length of tubing, e.g., a coiled or serpentine length of tubing, such that the media in the tubing spends sufficient time in the warming area 676 to reach a target temperature. In some examples, the warming flow path 674 can include a reservoir, such as a thin reservoir, to facilitate warming of the cell culture media. In some examples, the heating of the warming area 676 can be controlled such that the warming area 676 is heated only when cell culture media is being pumped into the fluidic circuit of the cell culture system, e.g., such that cell culture media that remains in the warming flow path 674 when no pumping is occurring is not warmed.

The operation of the temperature control system 650 can be controlled by a temperature controller 678. In some examples, such as shown in FIG. 16, the temperature controller 678 is incorporated into the temperature control system 650 itself and operates independently from the control of the cell culture system 100. In some examples, the computing device that controls the operation of the cell culture system 100 can also control the operation of the temperature control system 650.

In some examples, a pump (e.g., the pump 208a of FIG. 2) for pumping fresh cell culture media from the fresh media source 206 into the fluidic circuit can be housed in the interior space 654 of the temperature control system 650.

In some examples, the housing 652 of the temperature control system 650 can define multiple, distinct interior spaces, e.g., to allow for storage of material at different temperatures. For instance, multiple, distinct interior spaces can enable the storage of cell culture media and cell culturing reagents such as growth factor, serum, or other reagents, at appropriate temperatures.

In some examples, the temperature controlling module 658 can include a compartment for a cooling material, such as dry ice, e.g., in addition to or instead of the thermoelectric cooling module. In some examples, the cooling module can be a cooling system external to the housing 652, such as a main cooling system supplying cooling capacity (e.g., cooling fluid) through cooling lines to temperature control systems 650 for multiple cell culture systems 100.

Figure 18:
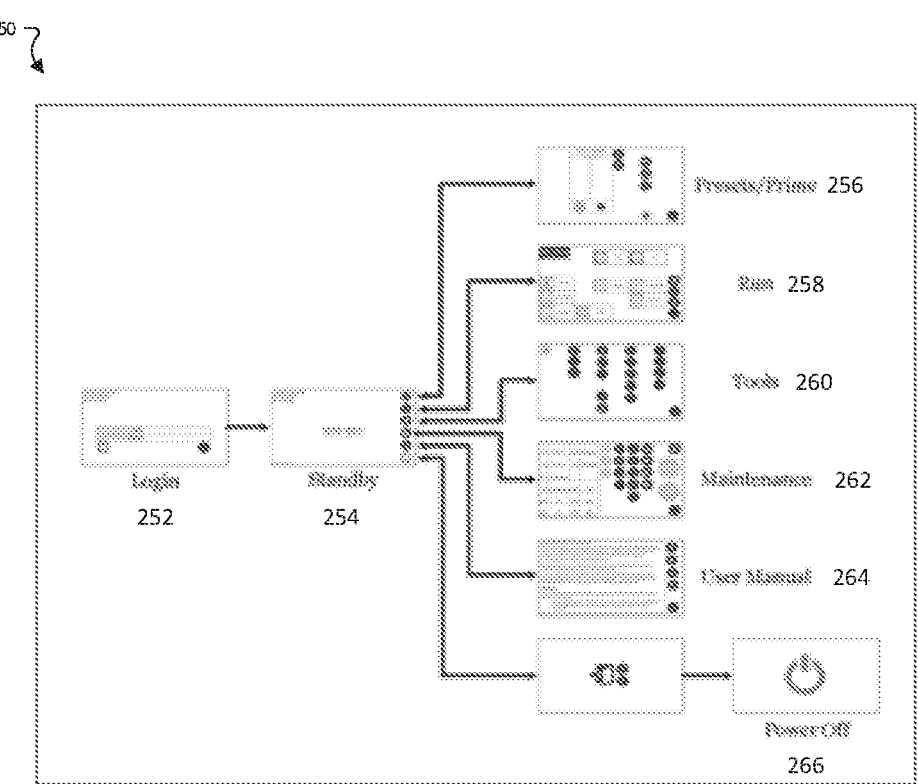
FIG. 18 is an overview of a user interface

FIG. 18 shows an example overview 250 of user interface views for a graphical user interface. For instance, the user interface can be developed on a PARLAY secure webserver platform and implemented as a set of web pages displayed on the user interface of the automated cell culture device or on the user interface of another computing device. The user interface, e.g., the user interface of the automated cell culture device, can be locally accessed by a user at the automated cell culture device or can be remotely accessed, e.g., through a connection from a remote computing device, by a user with secured authorization. In general, the user can provide instructions, e.g., by pressing or clicking icons on a touch screen user interface, to command operation of the automated cell culture system.

In the example of FIG. 18, an initial login screen 252 provides secured access to the user interface. When no cell culturing is underway, a standby screen 254 is displayed on the user interface. The user can access various pages, including a presets page 256 through which the user can preset operational parameters, such as thresholds; a run page 258 on which the user can monitor the status of an ongoing cell culture; a tools page 260 providing the user with access to system tools; a maintenance page 262 providing a person, such as an authorized maintenance engineer, with access to maintenance functionality; and a user manual page 264. The user can also power off the automated cell culture system through a power page 266 on the user interface.

FIGS. 19-22 are examples of screenshots that can be displayed on the user interface.

Figure 19:
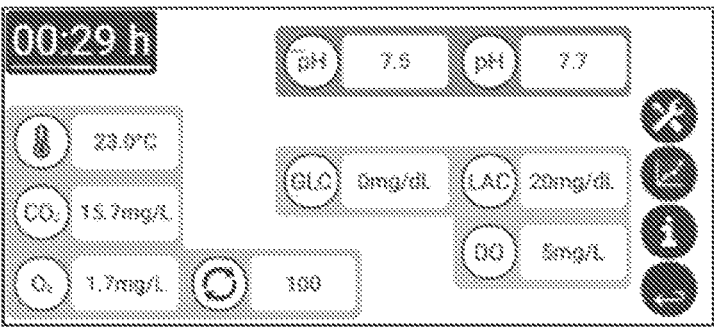
FIG. 19 is a screenshot.

FIG. 19 is an overview interface showing operational parameters of the automated cell culture system, such as elapsed time, temperature, atmospheric carbon dioxide concentration ($CO_2$), atmospheric oxygen concentration ($O_2$), pH (e.g., colorimetric pH and ionic pH values), glucose concentration in the cell culture media (GLC), lactate concentration in the cell culture media (LAC), dissolved oxygen partial pressure in the cell culture media (DO), and media flow rate. Other implementations of the view interface can display other parameters, or fewer parameters than those shown in FIG. 19.

Figure 20A:
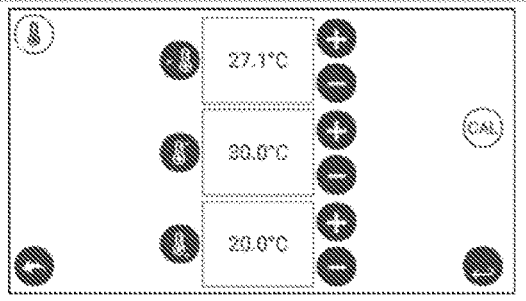
FIGS. 20A-20C are screenshots.
Figure 20B:
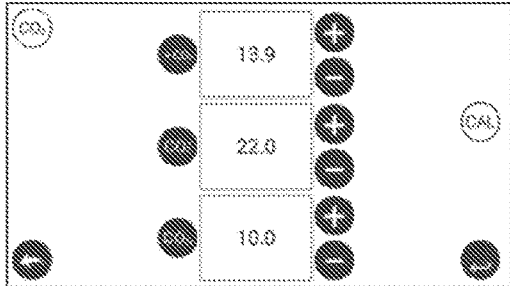
Figure 20C:
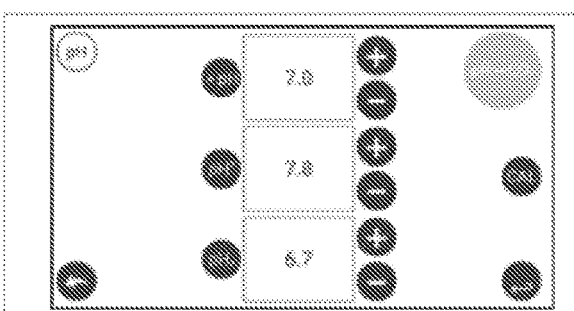

FIGS. 20A-20C are control interfaces for temperature, carbon dioxide concentration, pH, through which a user can set a target value, an upper threshold for triggering an alarm, and a lower threshold for triggering an alarm. Other parameters, such as oxygen concentration, glucose concentration, lactate concentration, dissolved oxygen, can be controlled through similar interfaces.

Figure 21:
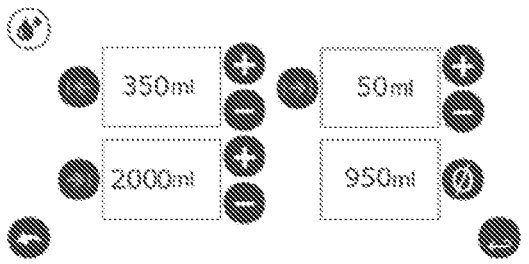
FIGS. 21 and 22 are screenshots.

FIG. 21 is a media exchange control interface through which a user can view and specify parameters for cell culture media exchange, including the amount of cell culture media in the reservoir, the volume of cell culture media to be exchanged, the capacity of the waste destination, and the amount of cell culture media transferred to the waste destination since the last time the waste destination was reset.

Figure 22:
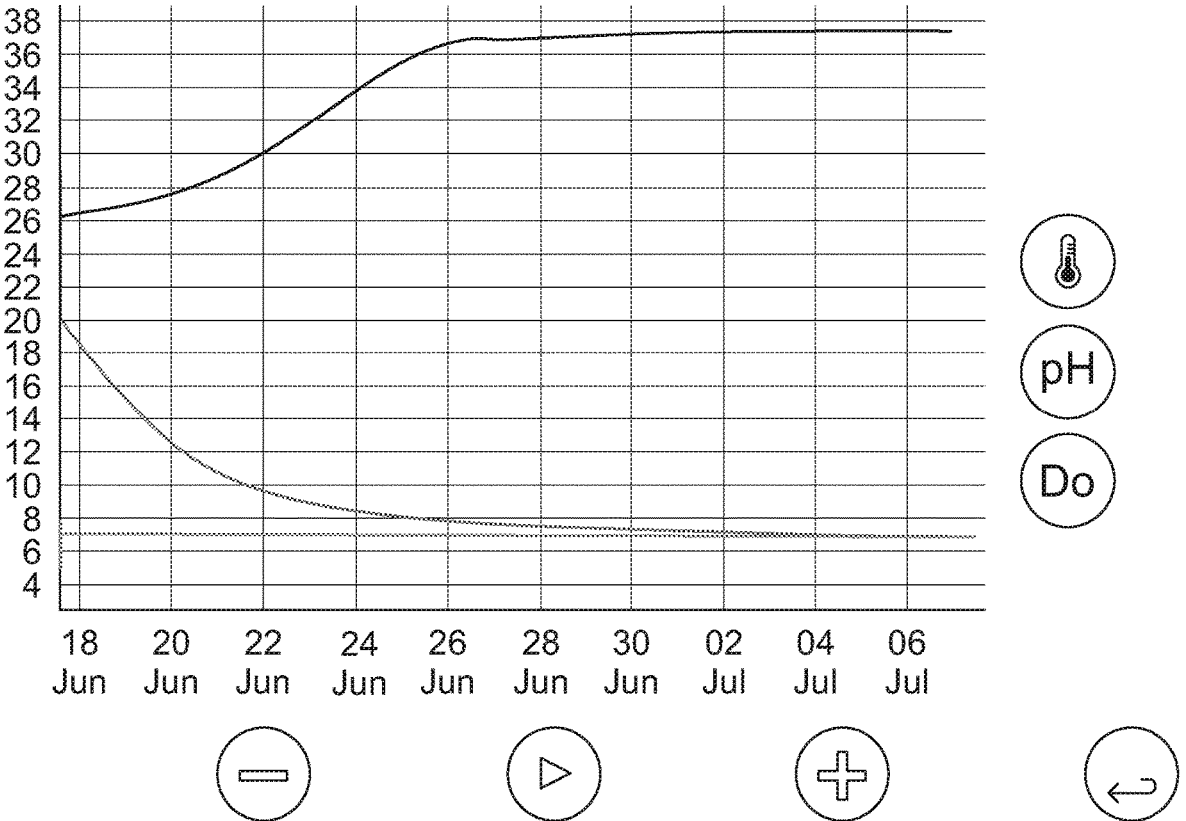

Referring to FIG. 22, the user interface can display parameters of the cell culture process in real time. For instance, the user interface can display a graph of temperature, pH, and dissolved oxygen as a function of time, e.g., as the cell culture progresses.

EXAMPLES

The following examples demonstrate the ability to culture viable cells in an automated cell culture system using hollow fiber cartridges.

Example 1—Cell Count, Viability, and Metabolic Profile of Cultured Cells

Jurkat, Clone E6-1, is a representative immortalized human T cell line that is widely used in immunological studies. Jurkat cells were cultured in an automated cell culture system using two, differently sized hollow fiber cartridges: small (20 mL of culture volume) and large (70 mL of culture volume). The cell count, viability, and metabolic profile of the cultured cells were determined. The basal medium was DMEM/F12 containing L-glutamine. The circulating media in the fluidic circuit and the intracapillary side of the hollow fiber cartridge contained 5% fetal bovine serum and antibiotics.

Inoculated Jurkat cells and fetal bovine serum were injected into the extracapillary side of the hollow fiber cartridge. Fetal bovine serum was added to the extracapillary side along with inoculated cells. 10 mL of fetal bovine serum was used for the small cartridge and 35 mL of fetal bovine serum was used for the large cartridge. 5% fetal bovine serum and antibiotics was circulated in the fluidic circuit and the intracapillary side of the hollow fiber cartridge at 100 mL/minute for seven days and increased to 200 mL/minute thereafter. Fetal bovine serum was refilled to the extracapillary side every three days. Glucose and lactate levels were monitored and calculated at mg/day. Cell number and viability were measured using Acridine Orange/Peroxide Iodide staining with a Countless FL II automated cell counter.

Figure 23A:
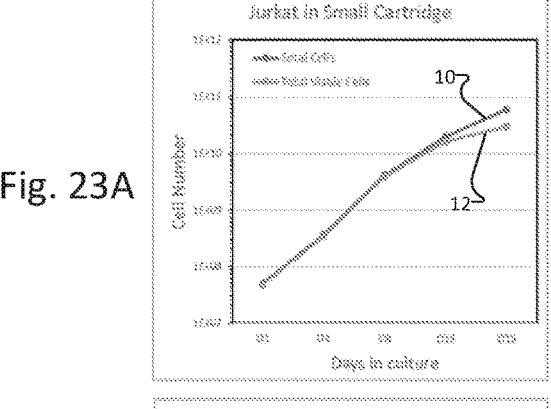
FIGS. 23A and 23B are plots of cell numbers.
Figure 23B:
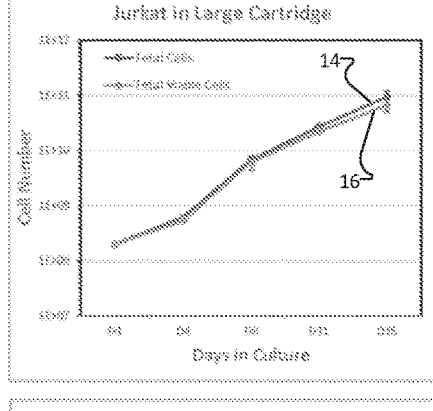

FIG. 23A shows the total cell count 10 and the count of viable cells 12 for the small cartridge; FIG. 23B shows the total cell count 14 and the count of viable cells 16 for the large cartridge. As can be seen from FIGS. 23A and 23B, the cell count increased steadily and nearly all of the cultured cells were viable.

Figure 24A:
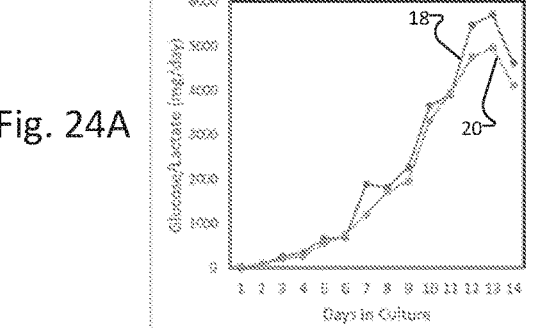
FIGS. 24A and 24B are plots of glucose and lactate concentration.
Figure 24B:
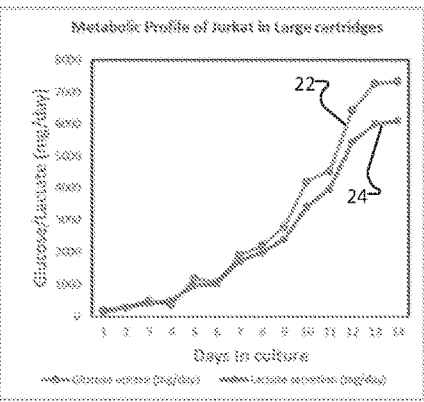

FIGS. 24A and 24B show metabolic profiles of the cultured cells for the small cartridge and the large cartridge, respectively. FIG. 24A shows that the glucose uptake 18 and lactate secretion 20 increased for the small cartridge until day 12, when the glucose uptake and lactate secretion began to decrease. FIG. 24B shows that the glucose uptake 22 and lactate secretion 24 increased for the large cartridge until day 13, when the glucose uptake and lactate secretion became substantially stable.

Example 2—Effect of Dissolved Oxygen Concentration on T Lymphocyte Culture

Primary human T lymphocytes were cultured in an automated cell culture system using hollow fiber cartridges to study the effect of dissolved oxygen concentration on cell expansion. Human T lymphocytes from a healthy donor were inoculated in the extracapillary side of the hollow fiber cartridges. In some cartridges, the cells were cultured in the presence of AIM-V media and human AB sera; in some cartridges, the cells were cultured in the presence of serum-free X-Vivo 15 media. Interleukin-2 (IL-2) was injected to the extracapillary side of the hollow fiber cartridge daily. For each cell culture media, dissolved oxygen levels were controlled to either an environmental level (~20% $O_2$) or a physiological level (~5% $O_2$). Cell number was estimated daily for each cartridge.

Figure 25A:
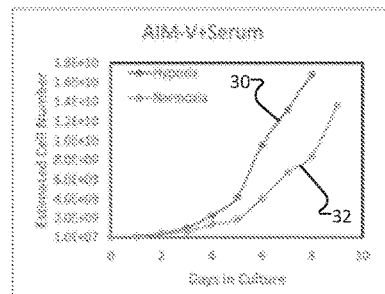
FIGS. 25A-25C are plots of cell expansion.
Figure 25B:
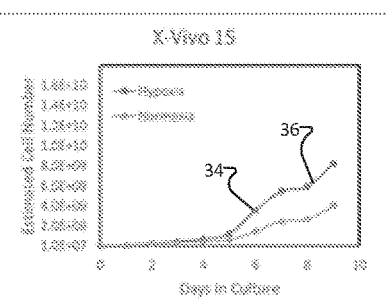
Figure 25C:
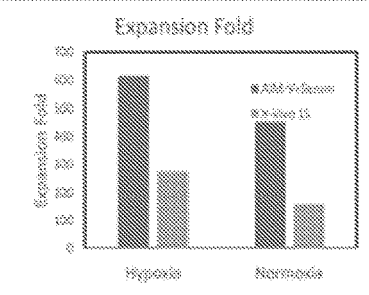

FIG. 25A shows the estimated cell count for hypoxia 30 (~5% $O_2$) and normoxia 32 (~20% $O_2$) for cells cultured in AIM-V media and human AB sera. FIG. 25B shows the estimated cell count for hypoxia 34 (~5% $O_2$) and normoxia 36 (~20% $O_2$) for cells cultured in serum-free X-Vivo 15 media. For both cell culture media, cell count was greater for cells cultured at hypoxia than at normoxia, although cell count was higher for cells cultured in AIM-V media and human AB sera than for cells cultured in serum-free media. FIG. 25C shows the expansion fold for both cell culture media and for cells cultured at hypoxia and normoxia. Consistent with FIGS. 25A and 25B, the expansion fold for both cell culture media was higher for cells cultured at hypoxia than at normoxia, and also higher for cells cultured in sera than for cells cultured in serum-free media. These results indicate that physiological oxygen levels greatly enhanced the cell growth speed and the final yield of human T lymphocytes in either serum-containing media or serum-free media.

Example 3—Expansion of T Lymphocytes in the Automated Cell Culture System

Human T lymphocytes were cultured in an automated cell culture system using a hollow fiber cartridge to validate the performance of the automated cell culture system and the hollow fiber cartridges.

In a first validation, human T lymphocytes were cultured in AIM-V media containing human AB sera. Human T lymphocytes from three healthy donors were activated with Dynabeads CD3/CD28 at a 1:1 ratio for three days and inoculated in the extracapillary side of a hollow fiber cartridge at a concentration of $2 \times 10^7$ cells per cartridge. Plain AIM-V media was circulated in the fluidic circuit and through the intracapillary side of the hollow fiber cartridge. 10 mL of Human AB sera was injected to the extracapillary side of the cartridge every three days. IL-2 was injected to the extracapillary side daily with a multiple rate at 1.5. Cell number and viability were measured with a Countess FL II cell counter. Subsets of T lymphocytes were stained with fluorescent dye labeled with antibodies targeting CD3, CD4, and CD9 markers and analyzed with BD Accuri C6 flow cytometry.

FIG. 26A shows the increase in cell count with time for cells from each of the three healthy donors. FIG. 26B shows the expansion fold and doubling time for cells from each of the three donors. FIG. 26C shows T-cell viability at inoculation and at harvest for cells from each of the three donors. FIG. 26D shows the CD3+ percentage for PBMCs, loaded cells, and harvested cells from each of the three donors. FIG. 26E shows the subset percentage of CD4+ and CD4− in CD3+ for PMBCs, loaded cells, and harvested cells for each of the three donors. These results validate that cells can be expanded and viability can be retained in the automated cell culture system.

In a second validation, human T lymphocytes were cultured in serum-free X-Vivo 15 media. Human T lymphocytes from three healthy donors were activated with Dynabeads CD3/CD28 at a 1:1 ratio for three days and inoculated in the extracapillary side of a hollow fiber cartridge at a concentration of $2 \times 10^7$ cells per cartridge. Plain X-Vivo 15 media were circulated in the fluidic circuit and through the intracapillary side of the hollow fiber cartridge. 10 mL of 1% Human albumin solution was injected to the extracapillary side of the cartridge every three days. IL-2 was injected to the extracapillary side daily with a multiple rate at 1.5. Cell number and viability were measured with a Countess FL II cell counter. Subsets of T lymphocytes were stained with fluorescent dye labeled with antibodies targeting CD3, CD4, and CD9 markers and analyzed with BD Accuri C6 flow cytometry.

Figures 27A, 27B, 27C, 27D, 27E:
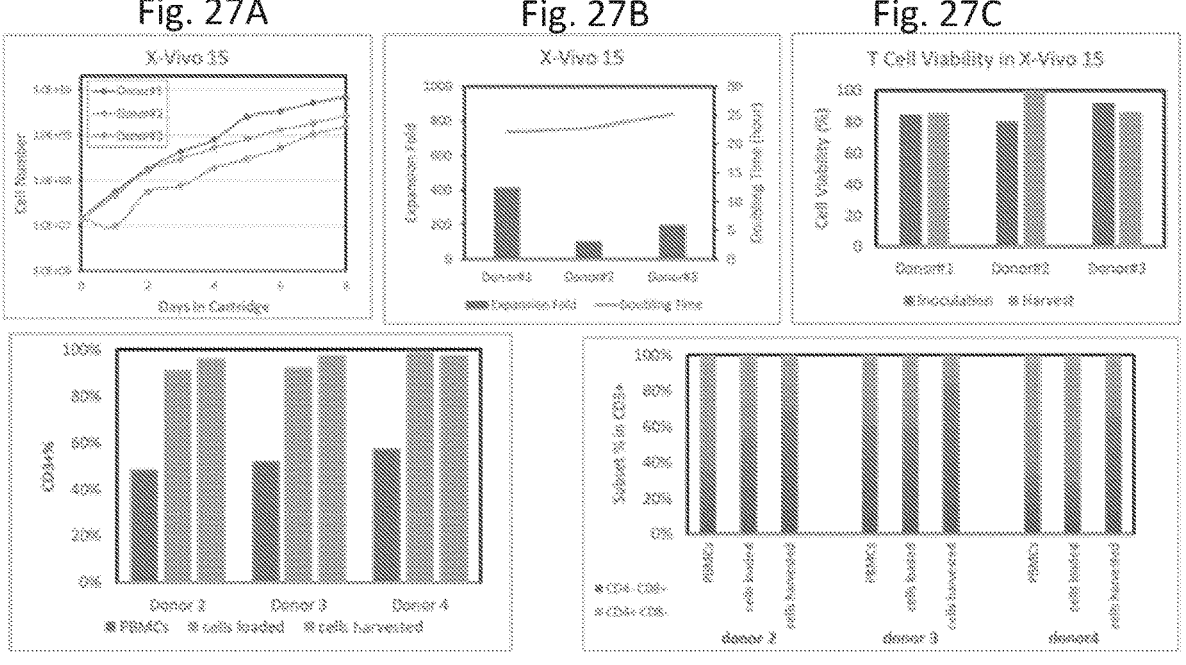
FIGS. 27A-27E are plots of cell expansion.

FIG. 27A shows the increase in cell count with time for cells from each of the three healthy donors. FIG. 27B shows the expansion fold and doubling time for cells from each of the three donors. FIG. 27C shows T-cell viability at inoculation and at harvest for cells from each of the three donors. FIG. 27D shows the CD3+ percentage for PBMCs, loaded cells, and harvested cells from each of the three donors. FIG. 27E shows the subset percentage of CD4+ and CD4− in CD3+ for PMBCs, loaded cells, and harvested cells for each of the three donors. These results validate that cells can be expanded and viability can be retained in the automated cell culture system.

A number of embodiments have been described. Nevertheless, it will be understood that various modifications may be made without departing from the spirit and scope of the invention. For example, some of the steps described above may be order independent, and thus can be performed in an order different from that described.

Other implementations are also within the scope of the following claims.

What is claimed is:

1. An automated cell culture system comprising:
a cell culture reactor comprising:
a housing;
a fluidic circuit for cell culture media, the fluidic circuit disposed in an interior of the housing, the fluidic circuit comprising:
a culture vessel for culturing cells in the cell culture media,
a reservoir for the cell culture media, the reservoir fluidically connected to the culture vessel, and
a pump configured to pump the cell culture media in the fluidic circuit; sensors disposed in the interior of the housing and configured to detect parameters indicative of a phase of the cell culture, wherein the parameters include culture solution volume, pH value, dissolved oxygen, glucose concentration, and lactic acid concentration;
a computing device comprising one or more processors and a memory for controlling an operation of the automated cell culture system, wherein the computing device is configured to:
automatically determine a phase of the cell culture based on the detected parameters, wherein the phase of the cell culture is selected from an initial growth phase, a rapid growth phase, and a plateau, and
automatically control a flow rate of cell culture media exchange within the cell culture reactor based on a comparison between at least the parameters indicative of the phase of the cell culture and a threshold, wherein the threshold depends on the phase of the cell culture, wherein the computing device is configured to control the flow rate of cell culture media exchange to be a first flow rate that maintains a first threshold volume of cell culture media when the cell culture is in the initial growth phase and a second flow rate that maintains a second threshold volume of cell culture media when the cell culture is in the rapid growth phase, wherein the first threshold volume during the initial growth phase is lower than the second threshold volume during the rapid growth phase, wherein the first flow rate during the initial growth phase is lower than the second flow rate during the rapid growth phase;

a supply system comprising:

a supply line, a first end of the supply line being connected to the fluidic circuit, and a second end of the supply line connectable to a source of cell culture media;

a supply pump coupled to the supply line; and a temperature control system comprising: a control housing, an interior space of the control housing configured to house the source of cell culture media, and a temperature controller configured to cool or warm the interior space of the control housing, wherein the computing device is configured to: control operation of the supply pump based on (i) an amount of the cell culture media in the reservoir and (ii) a pH of the cell culture media in the fluidic circuit; and a gas source fluidically coupled to the interior of the housing, and a gas flow controller coupled to the gas source, wherein the computing device is configured to: control operation of the gas flow controller based on the parameters indicative of the phase of the cell culture to maintain a concentration of carbon dioxide and a concentration of oxygen within preset ranges, wherein the concentration of oxygen is maintained at 5%.

2. The automated cell culture system of claim 1, comprising a rotational mount for the cell culture vessel.

3. The automated cell culture system of claim 1, comprising a heater disposed in the interior of the housing.

4. The automated cell culture system of claim 1, comprising a valve in the housing, in which the computing device is configured to control operation of the valve based on a concentration of gas in the interior of the housing.

5. The automated cell culture system of claim 1, wherein the computing device is configured to:

determine the phase of the cell culture in the culture vessel based on one or more of (i) the detected parameters and (ii) a history of the detected parameters; and control operation of the cell culture reactor based on the phase of the cell culture.

6. The automated cell culture system of claim 1, wherein the culture vessel comprises a hollow fiber cartridge.

7. The automated cell culture system of claim 1, wherein the computing device is configured to automatically maintain a hypoxic cell culture.

8. The automated cell culture system of claim 1, wherein the computing device is configured to check a weight of the source of cell culture media and confirm that there is sufficient cell culture media in the source to support a media exchange.

9. The automated cell culture system of claim 8, further comprising a waste destination connected to the fluidic circuit, wherein the computing device is configured to check an available capacity of the waste destination and confirm that there is sufficient capacity to support the media exchange.

10. The automated cell culture system of claim 9, wherein the computing device is configured to trigger an alert if there is not sufficient cell culture media in the source to support the media exchange or if there is not sufficient capacity in the waste destination to support the media exchange.

11. The automated cell culture of claim 2, further comprising an optical sensor configured to detect a rotational position of the cell culture vessel.

12. The automated cell culture of claim 11, wherein the computing device is configured to trigger a rotation of a rotational mount that the culture vessel is mounted on based on the comparison between the at least the parameters indicative of the phase of the cell culture and the threshold.

* * * * *